United States Patent
Bauer et al.

(10) Patent No.: US 8,735,366 B2
(45) Date of Patent: May 27, 2014

(54) PRE-MRNA TRANS-SPLICING MOLECULE (RTM) MOLECULES AND THEIR USES

(76) Inventors: Johann Bauer, Salzburg (AT); Lloyd G. Mitchell, Bethesda, MD (US)

( * ) Notice: Subject to any disclaimer, the term of this patent is extended or adjusted under 35 U.S.C. 154(b) by 439 days.

(21) Appl. No.: 13/056,449

(22) PCT Filed: Jul. 30, 2009

(86) PCT No.: PCT/EP2009/005538
§ 371 (c)(1),
(2), (4) Date: Apr. 14, 2011

(87) PCT Pub. No.: WO2010/012472
PCT Pub. Date: Feb. 4, 2010

(65) Prior Publication Data
US 2013/0059901 A1  Mar. 7, 2013

(30) Foreign Application Priority Data
Jul. 30, 2008 (EP) .................... 08013671

(51) Int. Cl.
*C12N 15/11* (2006.01)
*A01N 63/00* (2006.01)

(52) U.S. Cl.
USPC .................... 514/44 A; 424/93.21

(58) Field of Classification Search
None
See application file for complete search history.

(56) References Cited

U.S. PATENT DOCUMENTS

| | | | |
|---|---|---|---|
| 6,013,487 A * | 1/2000 | Mitchell | 435/91.3 |
| 6,083,702 A * | 7/2000 | Mitchell et al. | 506/9 |
| 6,280,978 B1 * | 8/2001 | Mitchell et al. | 435/91.3 |
| 2006/0246422 A1 * | 11/2006 | Mitchell et al. | 435/5 |

FOREIGN PATENT DOCUMENTS

| | | |
|---|---|---|
| WO | WO 00/09734 | 2/2000 |
| WO | WO 0009734 A2 * | 2/2000 |
| WO | WO 03/104416 | 12/2003 |
| WO | WO 2004/006678 | 1/2004 |

OTHER PUBLICATIONS

Dallinger et al., "Development of spliceosome-mediated RNA trans-splicing (SMaRT™) for the correction of inherited skin diseases", *Experimental Dermatology*, Feb. 2003, vol. 12, No. 1, pp. 37-46.
Liu et al., "Spliceosome-mediated RNA *trans*-splicing with recombinant adeno-associated virus partially restores cystic fibrosis transmembrane conductance regulator function to polarized human cystic fibrosis airway epithelial cells", *Human Gene Therapy*, Sep. 2005, vol. 16, No. 9, pp. 1116-1123.
Puttaraju et al., "Messenger RNA repair and restoration of protein function by spliceosome-mediated RNA *trans*-splicing", *Molecular Therapy*, Aug. 2001, vol. 4, No. 2, pp. 105-114.

* cited by examiner

*Primary Examiner* — Tracy Vivlemore
*Assistant Examiner* — Kate Poliakova-Georgan
(74) *Attorney, Agent, or Firm* — Saliwanchik, Lloyd & Eisenschenk

(57) ABSTRACT

The present invention relates to specific and markedly improved pre-mRNA trans-splicing molecule (RTM) molecules which are designed to correct specific genes expressed within cells to be targeted, and which are associated with epidermolysis bullosa, cystic fibrosis, pachyonychia congenital, and psoriasis or neurodermitis, as well as cancers of the skin. In particular, the RTMs of the present invention are genetically engineered to interact with a specific target pre-mRNA expressed in cells to be targeted so as to result in correction of genetic defects or reprogramming of gene expression responsible for a variety of different skin disorders.

19 Claims, 10 Drawing Sheets

SEQUENCE LISTING

<160> NUMBER OF SEQ ID NOS: 29

<210> SEQ ID NO 1
<211> LENGTH: 27
<212> TYPE: DNA
<213> ORGANISM: Homo sapiens

<400> SEQUENCE: 1
ggatccgtaa acccactggc tgcaatg        27

<210> SEQ ID NO 2
<211> LENGTH: 27
<212> TYPE: DNA
<213> ORGANISM: Homo sapiens

<400> SEQUENCE: 2
ggttacctgg aggagaggaa gggaaga                                               27

<210> SEQ ID NO 3
<211> LENGTH: 44
<212> TYPE: DNA
<213> ORGANISM: Homo sapiens

<400> SEQUENCE: 3
ccgtccccac ccacctgcac agctcttccc ttcctctcct ccag                            44

<210> SEQ ID NO 4
<211> LENGTH: 27
<212> TYPE: DNA
<213> ORGANISM: Homo sapiens

<400> SEQUENCE: 4
gagaacatta ttatagcgtt gctcgag                                               27

<210> SEQ ID NO 5
<211> LENGTH: 16
<212> TYPE: DNA
<213> ORGANISM: Homo sapiens

<400> SEQUENCE: 5
tcttcttttt tttctg                                                           16

<210> SEQ ID NO 6
<211> LENGTH: 18
<212> TYPE: DNA
<213> ORGANISM: Homo sapiens

<400> SEQUENCE: 6
caccatggtg agcaaggg                                                         18

<210> SEQ ID NO 7
<211> LENGTH: 25
<212> TYPE: DNA
<213> ORGANISM: Homo sapiens

<400> SEQUENCE: 7
gatatctctt acctcggcgc gactt                                                 25

<210> SEQ ID NO 8
<211> LENGTH: 24
<212> TYPE: DNA
<213> ORGANISM: Homo sapiens

<400> SEQUENCE: 8
gatatcgtga gtgtgtccag ggca                                                  24

<210> SEQ ID NO 9
<211> LENGTH: 26
<212> TYPE: DNA
<213> ORGANISM: Homo sapiens

<400> SEQUENCE: 9
gcggccgcct tcctcccgtc ttctcc                                                26

<210> SEQ ID NO 10
<211> LENGTH: 43
<212> TYPE: DNA
<213> ORGANISM: Homo sapiens

<400> SEQUENCE: 10

```
ggtacctctt cttttttttc tgcaggtgaa gttcgagggc gat          43
```

<210> SEQ ID NO 11
<211> LENGTH: 27
<212> TYPE: DNA
<213> ORGANISM: Homo sapiens

<400> SEQUENCE: 11

```
aagcttacac cagacaagtt ggtaatg                            27
```

<210> SEQ ID NO 12
<211> LENGTH: 43
<212> TYPE: DNA
<213> ORGANISM: Homo sapiens

<400> SEQUENCE: 12

```
caccgaattc atcgatgtta acgagaacat tattatagcg ttg          43
```

<210> SEQ ID NO 13
<211> LENGTH: 16
<212> TYPE: DNA
<213> ORGANISM: Homo sapiens

<400> SEQUENCE: 13

```
gctcacttgt acagct                                        16
```

<210> SEQ ID NO 14
<211> LENGTH: 26
<212> TYPE: DNA
<213> ORGANISM: Homo sapiens

<400> SEQUENCE: 14

```
ggatccgata tcatccgccc ctctcc                             26
```

<210> SEQ ID NO 15
<211> LENGTH: 28
<212> TYPE: DNA
<213> ORGANISM: Homo sapiens

<400> SEQUENCE: 15

```
cccgggaggt tgtggccata ttatcatc                           28
```

<210> SEQ ID NO 16
<211> LENGTH: 222
<212> TYPE: DNA
<213> ORGANISM: Homo sapiens

<400> SEQUENCE: 16

```
cttcctcccg tcttctccag ggtccccagg ttctccctgt gggcagagga ctcacatcag   60
cccaaacatt cactggtgtc tggctgcaag acactacctt gctagatttc agatgactgt  120 gactgtatttt ctgtgcctgt agctatggtt gtgtgtgtct tggagcatgg cctgtggccg  180
tctgagtgag ctgctacatg tctaggggtg tgcctgcata gg                    222
```

<210> SEQ ID NO 17
<211> LENGTH: 30
<212> TYPE: DNA
<213> ORGANISM: Homo sapiens

<400> SEQUENCE: 17

```
aacgagaaca ttattatagc gttgctcgag                         30
```

<210> SEQ ID NO 18

```
<211> LENGTH: 16
<212> TYPE: DNA
<213> ORGANISM: Homo sapiens

<400> SEQUENCE: 18
tcttcttttt tttctg                                                    16

<210> SEQ ID NO 19
<211> LENGTH: 15
<212> TYPE: DNA
<213> ORGANISM: Homo sapiens

<400> SEQUENCE: 19
gccactacgg caagc                                                     15

<210> SEQ ID NO 20
<211> LENGTH: 17
<212> TYPE: DNA
<213> ORGANISM: Homo sapiens

<400> SEQUENCE: 20
ccgtcttctc cagggtc                                                   17

<210> SEQ ID NO 21
<211> LENGTH: 19
<212> TYPE: DNA
<213> ORGANISM: Homo sapiens

<400> SEQUENCE: 21
agacggcatc gcagcttgg                                                 19

<210> SEQ ID NO 22
<211> LENGTH: 32
<212> TYPE: DNA
<213> ORGANISM: Homo sapiens

<400> SEQUENCE: 22
tctagagaat tctcagtcct gggcagtacc tg                                  32

<210> SEQ ID NO 23
<211> LENGTH: 18
<212> TYPE: DNA
<213> ORGANISM: Homo sapiens

<400> SEQUENCE: 23
atgtctgaga ggggccag                                                  18

<210> SEQ ID NO 24
<211> LENGTH: 19
<212> TYPE: DNA
<213> ORGANISM: Homo sapiens

<400> SEQUENCE: 24
ctcctgctcc tgttccacc                                                 19

<210> SEQ ID NO 25
<211> LENGTH: 18
<212> TYPE: DNA
<213> ORGANISM: Homo sapiens

<400> SEQUENCE: 25
caagggtgac cagggcga                                                  18

<210> SEQ ID NO 26
```

```
<211> LENGTH: 19
<212> TYPE: DNA
<213> ORGANISM: Homo sapiens

<400> SEQUENCE: 26
ccaaggagct tcagggtcc                                                    19

<210> SEQ ID NO 27
<211> LENGTH: 141
<212> TYPE: DNA
<213> ORGANISM: Homo sapiens

<400> SEQUENCE: 27
ccaaaggact ccctccagac actcatggag ggagtctttt ttcttttttct ttttcggaga      60 gacggtatca gcccactgca gcctggacct cctggactca agcgatcctc ccatctcagc     120
cttctgcata gctggaacta c                                               141

<210> SEQ ID NO 28
<211> LENGTH: 101
<212> TYPE: DNA
<213> ORGANISM: Homo sapiens

<400> SEQUENCE: 28
ctggagggga acctgcgttc ctcaaaggcg gccgtgtggt gtcgcatcca ctgaagcagc      60
agcagcacca gctcccggta ctcctgccag cgcagctgca g                         101

<210> SEQ ID NO 29
<211> LENGTH: 315
<212> TYPE: DNA
<213> ORGANISM: Homo sapiens

<400> SEQUENCE: 29
tccagcaaag tcagctccca atagtccgcc attgccagca tacatgccgc cttctgctgc      60
tgccccatag cctccgcctg ggccgatgtc agtgccatag ggaccctgt  ctcctgcagc     120 ttcactaaag gcaccgcctg cacccaggga gcctgcacca cctcctcctg tgctcatgga    180
agagctgtag gagctgcccc gcctgacaga tgagctgtgt gaggaggagt tgctacccca    240
actgtgggag gcatccgtgg acaggaggcg gctgtcccca gggggtccct gcggcccagg    300
agggcctggg gggcc                                                      315
```

PRE-MRNA TRANS-SPLICING MOLECULE (RTM) MOLECULES AND THEIR USES

CROSS REFERENCE TO A RELATED APPLICATION

This application is a National Stage Application of International Application Number PCT/EP2009/005538, filed Jul. 30, 2009; which claims priority to European Patent Application No. 08013671.6, filed Jul. 30, 2008; all of which are incorporated herein by reference in their entirety.

The present invention relates to specific and markedly improved pre-mRNA trans-splicing molecule (RTM) molecules which are designed to correct specific defective genes expressed within cells to be targeted, and which are associated with epidermolysis bullosa, cystic fibrosis, pachyonychia congenita, and autoimmune diseases, such as psoriasis or neurodermitis, as well as cancers of the skin. In particular, the RTMs of the present invention are genetically engineered to interact with a specific target pre-mRNA expressed in cells to be targeted so as to result in a treatment of a variety of different skin disorders and disorders of other epithelia.

The compositions of the invention further include recombinant nucleic acids and vectors systems capable of expressing the RTMs of the invention and cells expressing said RTMs. The methods of the invention encompass contacting the RTMs of the invention with specific target pre-mRNA expressed within cells to be targeted under conditions in which a portion of the RTM is trans-spliced to a portion of the target pre-mRNA to form a chimeric RNA molecule wherein the genetic defect in the specific gene has been corrected. The present invention is based on the successful trans-splicing of the pre-mRNA of a mammalian gene selected from the group of CFTR, integrins, TNF-alpha, interleukins, the immunoglobulin superfamily, kallikreins, matrix metalloproteinases, keratins, collagens, and laminins, thereby establishing the usefulness of trans-splicing for correction of skin diseases. The methods and compositions of the present invention can be used in gene therapy for treatment of specific disorders of the skin and other epithelia of the human body, such as epidermolysis bullosa, cystic fibrosis, pachyonychia congenita, and autoimmune diseases, such as psoriasis or neurodermitis, as well as cancers of the skin.

BACKGROUND OF THE INVENTION

RNA targeting is emerging as a powerful alternative to conventional gene replacement therapies for the treatment of genetic disorders. Although an emerging field, RNA modification has the potential to circumvent some of the shortcomings of standard gene therapy methods, including: (i) low efficiency of gene transfer; (ii) limitations on transgene size, specifically an inability to deliver genomic size loci; (iii) insertional mutagenesis and integration-associated events; and (iv) immune responses and toxicity due to vectors. Moreover, some disease situations could be more amenable to correction by RNA targeting, such as autosomal dominant diseases, where introduction of a functional gene does not address expression of the dominant mutant transcript.

Similarly, in disorders of RNA processing, such as aberrant splicing, it may be preferable to repair the endogenous splicing pattern, which could also correct multiple alternative isoforms.

More importantly, RNA targeting has unique potential for therapeutic modification of native mRNA transcripts within a normal regulatory environment. The potential of such approaches ranges from elimination of the mRNA in question to modification of the mature mRNA product by the removal or addition of natural elements or exons and to repair of the mRNA transcript by the addition of foreign mRNA elements to create a chimeric gene product.

The emergence of RNA trans-splicing has allowed methods to be developed for repairing genetic defects in the mature mRNA transcript. Trans-splicing is a natural process, although rare in mammals, which involves splicing between two separately transcribed mRNAs such that a composite transcript is produced. Manipulation of this process offers the potential for induction of isoform switching or the correction of dominant mutations by conversion to a wild type gene product.

The most common methodologies in current use are spliceosome mediated RNA trans-splicing (SMaRT) and ribozyme mediated trans-splicing.

In the SMaRT approach, an engineered pre-mRNA trans-splicing molecule (RTM) binds specifically to target pre-mRNA in the nucleus such that it triggers trans-splicing in a process mediated by the spliceosome (Puttaraju M, Jamison S F, Mansfield S G, Garcia-Blanco M A, Mitchell L G. Spliceosome-mediated RNA trans-splicing as a tool for gene therapy. Nat Biotechnol. 1999; 17:246-252). The major components of the RTM are a binding domain, a splicing domain, and a coding domain. The binding domain confers target specificity, whereas the splicing domain contains motifs necessary for the trans-splicing reaction to occur. The coding domain carries the portion of the wild-type cDNA, usually one or more exons, that are necessary to repair the targeted mutation. This repair is typically achieved by exon replacement and subsequent removal of the defective portion of the target pre-mRNA so that a functional gene product can be transcribed. Functional correction using spliceosome-mediated trans-splicing has been reported in several preclinical disease models, including cystic fibrosis (CF) (Liu X, Jiang Q, Mansfield S G, Puttaraju M, Zhang Y, et al. Partial correction of endogenous DeltaF508 CFTR in human cystic fibrosis airway epithelia by spliceosome-mediated RNA trans-splicing. Nat Biotechnol. 2002; 20: 47-52), haemophilia A (Chao H, Mansfield S G, Bartel R C, Hiriyanna S, Mitchell L G, et al. Phenotype correction of hemophilia A mice by spliceosome-mediated RNA trans-splicing. Nat Med. 2003; 9: 1015-1019), and X-linked immunodeficiency (Tahara M, Pergolizzi R G, Kobayashi H, Krause A, Luettich K, et al. Trans-splicing repair of CD40 ligand deficiency results in naturally regulated correction of a mouse model of hyper-IgM X-linked immunodeficiency. Nat Med. 2004; 10: 835-841).

The majority of trans-splicing studies to date have focused on restoration of function through replacement of the portion of the mRNA transcript containing the disease-causing mutation. However, trans-splicing also has potential application in treating disorders linked to aberrant splicing. The results in the case of human SMN (survival of motor neuron) (*Molecular Therapy* (2006) 13, S97 253. AAV Delivery of a Trans-Splicing RNA Re-Directs SMN2 Splicing and Results in Increased Full-Length SMN. Tristan H. Coady, Monir Shabab and Christian L. Lorson) and MAPT demonstrate that SMaRT can be used to manipulate alternative splicing and could have therapeutic application for those disorders that are a consequence of aberrant splicing (Rodriguez-Martin T, Garcia-Blanco M A, Mansfield S G, Grover A C, Hutton M, et al. Reprogramming of tau alternative splicing by spliceosome-mediated RNA trans-splicing: Implications for tauopathies. Proc Natl Acad Sci USA. 2005; 102: 15659-15664).

SMaRT has several advantages over conventional gene therapy. As the gene is repaired rather than introduced, the spatial and temporal expression of the gene should be controlled by endogenous regulation such that protein expression resembles that for normal individuals. As repair will only occur where the target transcript is expressed, adverse effects would not be anticipated in cells that were nonspecifically targeted during delivery. Trans-splicing can also address autosomal dominant disorders. As the level of repaired transcripts increases, the level of mutant transcript would be expected to decrease, which gene replacement does not address.

Another advantage is that because only a fragment of the gene needs to be replaced, the RTM constructs are easily accommodated in current vector systems.

Epidermolysis bullosa (EB) is the term applied to a heterogeneous group of inherited skin disorders in which minor trauma leads to blistering of skin and mucous membranes. Depending on the level of tissue cleavage, EB can be divided into three main groups: (i) EB simplex with blister formation occurring in the basal keratinocyte, (ii) junctional EB (JEB) with blister formation in the lamina lucida and (iii) EB dystrophicans with blister formation below the lamina densa.

JEB patients are divided into two main groups, Herlitz JEB and generalized atrophic benign EB (GABEB). Patients diagnosed with the former disease usually die within their first year of life, whereas the latter diagnosis is associated with a better prognosis and a tendency for improvement during life. Initial observations describing reduced expression of bullous pemphigoid antigen 2 (BPAG2), identified as type XVII collagen, in patients suffering from GABEB were followed by the identification of mutations in the gene coding for BPAG2 (Col17A1). To date, a number of different mutations in the Col17A1 have been identified leading to the establishment of a mutation database, which has facilitated the analysis of the effects of specific mutations on the clinical presentation of nH-JEB. For example, it has been determined that stop codon mutations or mutations leading to downstream stop codons on both alleles are associated with the original "GABEB" phenotype.

In addition, EB simplex with late onset muscular dystrophy (EBS-MD) patients have been characterized with mutations in the plectin gene. Some of these patients feature compound heterozygosity for a three base-pair insertion at position 1287 (1287ins3) leading to the insertion of leucine as well as missense mutation, Q1518X causing the insertion of a stop codon in the plectin coding region (Bauer, J W et al., 2001 *Am J Pathol* 158: 617-625).

There is a variety of different methods to replace or repair the genes targeted in gene therapy, depending on the underlying genetic abnormalities. Current approaches include gene replacement, gene correction, gene silencing, and gene targeting (Zahid and Brownell 2007). In the case of recessive loss-of-function mutations gene replacement through simple reintroduction of a functional wild type copy of this gene by viral or non-viral insertion may be sufficient for correction (Khavari P. A., Rollman O., & Vahlquist A. (2002) Cutaneous gene transfer for skin and systemic diseases. *Journal of Internal Medicine* 252, 1-10.). Recently, ex vivo gene therapy successfully treated a patient with junctional EB by the transduction of the respective cDNA carried by a viral vector (Mavilio F. et al. (2006) Correction of junctional epidermolysis bullosa by transplantation of genetically modified epidermal stem cells. *Nature Medicine* 12, 1397-1402). This study demonstrates the feasibility of cDNA-complementing approaches in cases of knockout mutations. However, supplementation with a highly expressed and functional gene is inadequate to neutralize dominant negative gain-of-function mutations. Promising strategies have been developed to overcome this problem (Laimer M. et al. (2006) Current approaches to cutaneous gene therapy. *Expert Rev. Dermatol.* 1, 833-853. 2006).

In skin gene therapy, most efforts to date have attempted to deliver full length cDNA copies of the affected gene using retroviral vectors. However, the delivery of full length cDNA in skin therapy is often limited by the size of the mRNA (or cDNA), for example, the plectin mRNA is 14.8 kb, the type VII collagen mRNA is 9.2 kb and the type XVII collagen mRNA is 6.5 kb. The size of these genes, mutated in patients with various forms of EB, and their regulatory elements are beyond the capacity of delivery systems suitable for skin gene therapy using retroviral or adeno-associated viral vectors. Therefore, it would be advantageous to reduce the size of the therapeutic sequence that has to be delivered.

It is also critical that the genes implicated in cutaneous blistering disorders and targeted for gene therapy are only expressed by keratinocytes of a specific epidermal layer. For example, ectopic expression of such genes may lead to disordered epithelial polarity. One possible way to address the problem of keratinocyte specific expression is to use specific regulatory elements to direct transgene expression. However, the use of such promoters further increases the size of the insert in a therapeutic vector.

For the Col17A1 gene, alternative approaches to gene correction have been described. Notably, there are natural mechanisms by which mutations have been corrected in the Col17A1 gene validating the concept of gene therapy. For example, Jonkman et al., (1997, *Cell* 88:543-551) reported on a patient who had patches of normal appearing skin in a symmetrical leaf-like pattern on the upper extremities. The underlying mutations in the Col17A1 gene had been identified as R1226X paternally, and 1706delA, maternally. In the clinical unaffected areas of the skin about 50% of the basal cells were expressing type XVII collagen at a reduced level due to a mitotic gene conversion surrounding the maternal mutation, thus leading to loss of heterozygosity in this area. These observations suggest that expression of less than 50% of full length type XVII collagen is sufficient to correct the phenotypic expression of nH-JEB. In addition, a partly successful gene correction by the keratinocyte splicing machinery has been described in patients with the homozygous R785X mutation in the Col17A1 gene (Ruzzi L et al., 2001 *J. Invest Dermatol* 116: 182-187). In these patients, the exclusion of exon 33, harboring the mutation, leads to an unusual mild phenotype, although there is only 3-4% of detectable type XVII collagen protein. Similar in frame skipping of exons has also been reported for patients with mutations in the Col17A1 and LAMB3 gene.

Functional RNA repair by SMaRT has been reported in a variety of in vitro, ex vivo, and in vivo studies. In each of these studies, a RTM carrying a portion of the full-length cDNA and a binding domain designed to target a specific intron in the endogenous pre-mRNA was used for the correction of a genetic disorder. Proof of principle for mRNA repair by trans-splicing has been presented by Liu et al., showing functional correction of the predominant cystic fibrosis transmembrane conductance regulator (CFTR) mutation ΔF508 in an in vitro model (Liu, X, M. Luo, L. N. Zhang, Z. Yan, R. Zak, W. Ding, G. S. Mansfield, L. G. Mitchell, and J. F. Engelhardt. Spliceosome-Mediated RNA Trans-splicing with rAAV Partially Restores CFTR Function to Polarized Human CF Airway Epithelial Cells. Human Gene Therapy 16(9):1116-23, 2005). The feasibility of SMaRT to be used in skin gene therapy has been established in the laboratory of the present inventors in a double transfection system for the well characterized mutation 4003delTC in the collagen XVII gene in normal human keratinocytes and an immortalized GABEB cell-line (Dallinger G. et al. (2003) Development of spliceosome-mediated RNA trans-splicing (SMaRT) for the correction of inherited skin diseases. Experimental Dermatology 12, 37-46). With this approach the inventors have shown that keratinocytes are capable of trans-splicing. Further, Wally et al. recently showed that trans-splicing in the plectin gene in patient fibroblasts increased the level of functional plectin protein by 58% in vitro (Wally V. et al. (2008) 5' trans-splicing repair of the PLEC1 gene. J. Invest Dermatol. 128, 568-574). In addition to successful reports of the utility of SMaRT as an RNA-repair technology in vitro, functional correction using trans-splicing has been shown in several preclinical models of human diseases, such as cystic fibrosis (Puttaraju M. et al. (2001) Messenger RNA repair and restoration of protein function by spliceosome-mediated RNA trans-splicing. Molecular Therapy 4, 105-114), hemophilia A (Chao H. et al. (2003) Phenotype correction of hemophilia A mice by spliceosome-mediated RNA trans-splicing. Nat. Med. 9, 1015-1019), and Xlinked immunodeficiency (Tahara M. et al. (2004) Trans-splicing repair of CD40 ligand deficiency results in naturally regulated correction of a mouse model of hyper-IgM X-linked immunodeficiency. Nat. Med. 10, 835-841).

U.S. Pat. Nos. 6,083,702, 6,013,487, 6,280,978, 7,399,753 and EP 0 883 344 (all incorporated by reference in their entireties) describe the use of RTMs to mediate a trans-splicing reaction by contacting a target precursor mRNA to generate novel chimeric RNAs.

WO 2004/006678 describes specific RTM molecules designed to correct specific defective genes expressed within cells of the skin and associated with skin disorders. The specific RTMs may be used to treat a variety of different skin disorders such as genodermatoses including epidermal fragility disorders, keratinization disorders, hair disorders, pigmentation disorders and cancers.

Despite the progress in the field of RTM molecules, and while co-transfection of mini-gene targets and RTMs have obtained reasonable levels of trans-splicing in vitro, for endogenous pre-mRNA or stably expressed pre-mRNA in vivo, splicing efficiency is lower.

It is therefore an object of the present invention to provided new, specific, and markedly improved RTM molecules that are designed to correct specific defective genes expressed within cells to be targeted, and which are associated with epidermolysis bullosa, cystic fibrosis, pachyonychia congenita, and autoimmune diseases, such as psoriasis or neurodermitis as well as cancers of the skin. It is a further object of the present invention, to provide for further improved methods for the treatment of disorders of the skin, such as epidermolysis bullosa, cystic fibrosis, pachyonychia congenita, and autoimmune diseases, such as psoriasis or neurodermitis, as well as cancers of the skin, based on RTMs.

In a first aspect of the present invention, this object is solved through providing a pre-mRNA trans-splicing molecule (RTM), comprising a) at least one binding domain that targets binding of the nucleic acid molecule to a pre-mRNA expressed within a cell; b) at least one splicing domain containing motifs necessary for the trans-splicing reaction to occur, and c) at least one coding domain, wherein said coding domain encodes for at least one exon of a mammalian gene selected from the group of CFTR, integrins, TNF-alpha, interleukins, the immunoglobulin superfamily, kallikreins, matrix metalloproteinases, keratins, collagens, and laminins.

The general design, construction and genetic engineering of RTMs and demonstration of their ability to successful mediate spliceosome mediated trans-splicing reactions within the cell are described in detail in U.S. Pat. Nos. 6,083, 702, 6,013,487, 7,399,753 and 6,280,978 as well as patent applications with the U.S. Ser. Nos. 09/756,095, 09/756,096, 09/756,097 and 09/941,492, the disclosures of which are incorporated by reference in their entirety herein.

In brief, an RTM molecule is designed to carry a binding domain (BD) complementary to and in antisense orientation to an intron sequence of the target pre-mRNA, to suppress target cis-splicing while enhancing trans-splicing between the RTM and the target (Mansfield et al. 2000). A RTM molecule further consists of a splicing domain, comprising a strong conserved branch point (BP) sequence, a polypyrimidine tract (PPT), and a 3' acceptor splice site (ss). A spacer sequence separates the splicing domain from the target binding domain. And finally a RTM comprises a coding domain with the part of the wild type coding sequence to be trans-spliced to the target pre-mRNA (FIG. 2). The coding domain can be a single exon, multiple exons or an entire coding sequence.

The BD brings specificity to trans-splicing by binding specifically to the endogenous target pre-mRNA, whereas the splicing and coding domains provide essential consensus motifs that are recognized by the spliceosome and make the trans-splicing reaction actually happen. The use of BP and PPT follows consensus sequences which are needed for performance of the two phosphoryl transfer reaction involved in cis-splicing and, presumably, also in trans-splicing (Kramer 1996). These reactions, catalyzed by the spliceosome, must excise the introns precisely in order to produce functional mRNAs. In a manner similar to the RNA cis-splicing processes, the binding domain and splicing domain sequences of the RTM RNA are excised after trans-splicing and are not retained in the reprogrammed final mRNA products.

The methods of the invention encompass contacting the RTMs of the invention with a target pre-mRNA, under conditions in which a portion of the RTM is trans-spliced to a portion of the target pre-mRNA to form a novel RNA molecule that is further processed to form mRNA that functions to express said target mRNA.

The target binding domain of the RTM endows the RTM with a binding affinity for the target pre-mRNA. As used herein, a target binding domain is defined as any molecule, i.e., nucleotide, protein, chemical compound, etc., that confers specificity of binding and anchors the pre-mRNA closely in space to the synthetic RTM so that the spliceosome processing machinery of the nucleus can trans-splice a portion of the synthetic RTM to a portion of the pre-mRNA.

The target binding domain of the RTM may contain multiple binding domains which are complementary to and in anti-sense orientation to the targeted region of the selected target pre-mRNA. The target binding domains may comprise up to several thousand nucleotides. In preferred embodiments of the invention the binding domains may comprise at least 10 to 30 and up to several hundred or more nucleotides. The specificity of the RTM may be increased significantly by increasing the length of the target binding domain. For example, the target binding domain may comprise several hundred nucleotides or more. Absolute complementarity, although preferred, is not required. A sequence "complementary" to a portion of an RNA, as referred to herein, means a sequence having sufficient complementarity to be able to hybridize with the target pre-mRNA, forming a stable duplex. The ability to hybridize will depend on both the degree of complementarity and the length of the nucleic acid (See, for example, Sambrook et al., 1989, Molecular Cloning, A Laboratory Manual, 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch or length of duplex by use of standard procedures to determine the stability of the hybridized complex.

Preferred is an RTM according to the present invention, wherein said binding domain comprises at least part of a sequence complementary to an intron or an exon of a mammalian gene, and preferably at least part of a sequence complementary to an exon of a mammalian gene.

It was demonstrated in the context of the present invention, and in contrast to current knowledge and as highlighted in the state of the art, such as in WO 00/009734, that binding to exonic regions of a gene, i.e. a binding domain targeting an exonic sequence of a gene (as shown for the genes PLEC1 and COL17A1, example 3) can be achieved with a higher efficiency than binding to intronic regions. Thereby, the experiments using the genes PLEC1 and COL17A1 provide a proof of concept that exonic sequences provide powerful and effective starting points for a design and the use of PTMs according to the present invention.

Preferred is an RTM according to the present invention that further comprises at least part of the respective intron upstream of the at least one exon that is functioning as the binding domain.

Nevertheless, the RTMs of the invention may also include at least one of the following features: (a) binding domains targeted to intron sequences in close proximity to the 3' or 5' splice signals of the target intron, (b) mini introns, and (c) intronic or exonic enhancers or silencers that would regulated the trans-splicing (Garcia-Blanco et al (2004) Nature Biotechnology, 22, 535-546. The RTMs of the invention may further comprise one or more spacer regions to separate the RNA splice site from the target binding domain.

Binding may also be achieved through other mechanisms, for example, through triple helix formation, aptamer interactions, antibody interactions or protein/nucleic acid interactions such as those in which the RTM is engineered to recognize a specific RNA binding protein, i.e., a protein bound to a specific target pre-mRNA.

3' RTM molecules also contain a 3' splice region that includes a branchpoint sequence and a 3' splice acceptor AG site and/or a 5' splice donor site. The 3' splice region may further comprise a polypyrimidine tract. 5' RTMs contain a 5' splice site region, including a GU splice donor site. Consensus sequences for the 5' splice donor site and the 3' splice region used in RNA splicing are well known in the art (See, Moore, et al., 1993, The RNA World, Cold Spring Harbor Laboratory Press, p. 303-358). In addition, modified consensus sequences that maintain the ability to function as 5' donor splice sites and 3' splice regions may be used in the practice of the invention. Briefly, the 5' splice site consensus sequence is AG/GURAGU (where A=adenosine, U=uracil, G=guanine, C=cytosine, R=purine and /=the splice site). The 3' splice site consists of three separate sequence elements: the branchpoint or branch site, a polypyrimidine tract and the 3' consensus sequence (YAG). The branch point consensus sequence in mammals is YNYURAC (Y=pyrimidine; N=any nucleotide). The underlined A is the site of branch formation. A polypyrimidine tract is located between the branch point and the splice site acceptor and is important for different branch point utilization and 3' splice site recognition. Recently, pre-mRNA introns referred to as U12-dependent introns, many of which begin with the dinucleotide AU and end in the dinucleotide AC, have been described. U12-dependent intron sequences as well as any sequences that function as splice acceptor/donor sequences may also be used to generate the RTMs of the invention.

A spacer region to separate the RNA splice site from the target binding domain may also be included in the RTM. The spacer region may be designed to include features such as (i) stop codons which would function to block translation of any unspliced RTM and/or (ii) sequences that enhance trans-splicing to the target pre-mRNA.

During experiments that were performed by the inventors in the context of the present invention, it was found that these genes are suitable as effective targets for pre-mRNA trans-splicing, in order to treat the diseases as mentioned herein. In the context of the present invention, "treatment" shall mean any of prevention, delay of outbreak, reducing the severity of the disease symptoms, and/or removing the disease symptoms (to cure) in a given patient.

The methods of the invention encompass contacting the RTMs of the invention with a target pre-mRNA, under conditions in which a portion of the RTM is spliced to the target pre-mRNA to form a novel mRNA of the targeted gene, in order to correct mRNA, Alternatively, a pre-miRNA (see below) can be formed, which is designed to reduce the expression of a target mRNA. Thus, the methods and compositions of the invention can be used to treat diseases/pathologies associated with specific mutations and/or gene expression. For example, the methods and compositions of the invention can be used to "correct" mutations or to reduce the expression of genes associated with diseases of skin cells as described herein, such as proliferative disorders such as cancer. In another preferred embodiment, the methods and compositions of the invention can also be used to reprogram one specific gene into another. As one example, the addition of Interleukin 10 exons to the ICAM-1 gene gives two aspects of reprogramming gene expression and thus treating autoimmune diseases such as psoriasis. On the one hand, a gene crucial to the pathogenesis of psoriasis in endothelial cells is downregulated, at the same time a immunosuppressive interleukin is produced by the same ICAM-1 gene. The resulting peptide is a hybrid of exon 1 of ICAM-1 and exon 2-5 of IL-10. As another example, the addition of HSV-thymidin kinase into MMP-9 allows for the improved treatment of tumors of the skin (based on the publication of Siegele et al. eIF4E-targeted suicide gene therapy in a minimal residual mouse model for metastatic soft-tissue head and neck squamous cell carcinoma improves disease-free survival. J Surg Res. 2008 July; 148(1):83-9).

As already discussed above, the present invention provides a pre-mRNA trans-splicing molecule (RTM), comprising, as one part, at least one coding domain, wherein said coding domain encodes for at least one exon of a mammalian gene selected from the group of CFTR, integrins, keratins, collagens, and laminins. The present invention further provides a pre-mRNA trans-splicing molecule (RTM), comprising, as one part, at least one coding domain, wherein said coding domain encodes for at least one exon of a mammalian gene selected from the group of CFTR, integrins, keratins, collagens, and laminins together with a reprogramming part as described above, wherein TNF-alpha, interleukins, the immunoglobulin superfamily, kallikreins, matrix metalloproteinases can be used as "target genes" as well as source of the RTM (for example ICAM-1 as a target and interleukin-10 as RTM; MMP-9 as a target and HSV thymidine kinase as RTM).

Preferred is the use of an RTM of the present invention derived from plectin, collagens and keratins for the treatment of epidermolysis bullosa and related diseases, such as muscular dystrophy (cf. Pfendner, E.; Uitto, J.: Plectin gene mutations can cause epidermolysis bullosa with pyloric atresia. *J. Invest. Derm.* 124: 111-115, 2005, and references as cited therein, Varki, R.; Sadowski, S.; Uitto, J.; Pfendner, E.: Epidermolysis bullosa. II. Type VII collagen mutations and phenotype-genotype correlations in the dystrophic subtypes. *J. Med. Genet.* 44: 181-192, 2007, and references as cited therein; Jonkman, M. F.; Pas, H. H.; Nijenhuis, M.; Kloosterhuis, G.; van der Steege, G.: Deletion of a cytoplasmic domain of integrin beta-4 causes epidermolysis bullosa simplex. *J. Invest. Derm.* 119: 1275-1281, 2002, and references as cited therein).

Also preferred is the use of an RTM of the present invention derived from CFTR, for the treatment of cystic fibrosis.

RTMs of the present invention derived from kallikreins, and matrix metalloproteinases (such as MMP9) and can be composed so as to function as constructs for targeting said genes in order to treat skin tumors and other cancers by introducing suicide or apoptosis genes (or functional fragments thereof), such as, for example, HSV-thymidin kinase. Other examples of these therapeutic genes are described in the literature (for example in Revil T, Shkreta L, Chabot B. Pre-mRNA alternative splicing in cancer: functional impact, molecular mechanisms and therapeutic perspectives Bull Cancer. 2006 Sep. 1; 93 (9): 909-19.).

Further preferred RTMs of the present invention can be derived from keratin 6, 16 or 17 for the treatment of pachyonychia congenita and related diseases. Further preferred RTMs of the present invention can be derived from Interleukin-10 and 12, and are used for the treatment of psoriasis or neurodermitis and related autoimmune diseases. Here, RTMs are preferably targeted to ICAM-1, VCAM-1 and/or TNF-a.

Preferred RTMs of the present invention can comprise coding domains encoding for one or more exons that can be derived from one or more of the following tables. In the tables, the names and Database accession numbers are given for preferred genes from which the exons as included in the RTMs according to the present invention can be composed. As an example, an RTM of the present invention can comprise between 1 and 7 exons of the gene KRT17 (Database accession number NM_000422). Mutations or other defects in said gene are related to the disease pachyonychia congenita (Terrinoni, A.; Smith, F. J. D.; Didona, B.; Canzona, F.; Paradisi, M.; Huber, M.; Hohl, D.; David, A.; Verloes, A.; Leigh, I. M.; Munro, C. S.; Melino, G.; McLean, W. H. I.: Novel and recurrent mutations in the genes encoding keratins K6a, K16 and K17 in 13 cases of pachyonychia congenita. *J. Invest. Derm.* 117: 1391-1396, 2001). The constructs derived from the tables below can preferably be modified as further described below.

The person of skill will understand that the database accession numbers as given may contain sequence errors and/or sequencing errors that require a later correction of said sequence. The present invention is intended to also encompass all these putative corrections, and the person of skill is able to take these corrections into account when working the present invention. The sequences as provided by the database accession numbers may also be used to search for homologous sequences in the same or another mammalian organism.

TABLE 1

Basis for constructs derived from keratins

| Gene | Database accession number | DNA size | mRNA size | Exons | Entrez gene ID | Related disease |
|---|---|---|---|---|---|---|
| KRT1 | NM_006121 | 5.73 Kb | 2507 bp | 9 | 3848 | |
| KRT10 | XM_352919 | 3.67 Kb | 1542 bp | 9 | 3858 | epidermolytic |
| KRT12 | NM_000223 | 5.91 Kb | 1867 bp | 8 | 3859 | hyperkeratosis; keratosis palmaris et plantaris Meesmann corneal dystrophy |
| KRT13 | NM_002274 | 4.63 Kb | 1689 bp | 7 | 3860 | |
| KRT14 | NM_000526 | 4.61 Kb | 1634 bp | 8 | 3861 | epidermolysis bullosa simplex, Dowling-Meara, Koebner |
| KRT15 | NM_002275 | 5.14 Kb | 1709 bp | 8 | 3866 | |
| KRT16 | NM_005557 | 2.99 Kb | 1655 bp | 8 | 3868 | focal non-epidermolytic palmoplantar keratoderma |
| KRT17 | NM_000422 | 5.11 Kb | 1498 bp | 8 | 3872 | epidermolysis bullosa simplex, Dowling-Meara/Kobner/Weber-Cockayne types |
| KRT18 | NM_000224 | 3.78 Kb | 1408 bp | 7 | 3875 | |
| KRT19 | NM_002276 | 4.68 Kb | 1381 bp | 6 | 3880 | |
| KRT2 | | 7.62 Kb | 2459 bp | 9 | 3849 | |
| KRT20 | NM_019010 | 9.28 Kb | 1735 bp | 8 | 54474 | |
| KRT23 | NM_015515 | 14.88 Kb | 2147 bp | 9 | 25984 | |
| KRT24 | NM_019016 | 5.76 Kb | 1879 bp | 8 | 192666 | |
| KRT25 | | 7.29 Kb | 1684 bp | 8 | | |
| KRT26 | | 5.92 Kb | 1748 bp | 8 | | |
| KRT27 | | 5.72 Kb | 1635 bp | 8 | | |
| KRT28 | | 7.7 Kb | 1692 bp | 8 | | |
| KRT3 | NM_057088 | 6.34 Kb | 2232 bp | 9 | 3850 | |
| KRT31 | | 3.87 Kb | 1616 bp | 7 | | |
| KRT32 | | 7.58 Kb | 2005 bp | 7 | | |
| KRT33A | | 4.69 Kb | 1252 bp | 7 | | |

TABLE 1-continued

Basis for constructs derived from keratins

| Gene | Database accession number | DNA size | mRNA size | Exons | Entrez gene ID | Related disease |
|---|---|---|---|---|---|---|
| KRT33B | | 6.3 Kb | 1621 bp | 7 | | |
| KRT34 | | 4.72 Kb | 1713 bp | 7 | | |
| KRT35 | | 4.45 Kb | 1688 bp | 8 | | |
| KRT36 | | 3.73 Kb | 1688 bp | 7 | | |
| KRT37 | | 4.3 Kb | 1718 bp | 7 | | |
| KRT38 | | 4.98 Kb | 2837 bp | 7 | | |
| KRT4 | NM_002272 | 7.25 Kb | 1824 bp | 9 | 3851 | |
| KRT5 | NM_002275 | 5.14 Kb | 1709 bp | 8 | | |
| KRT5 | NM_000424 | 5.88 Kb | 2301 bp | 9 | 3852 | |
| KRT6A | NM_005554 | 6.04 Kb | 2270 bp | 9 | 3853 | |
| KRT6B | NM_005555 | 5.41 Kb | 2217 bp | 9 | 3854 | |
| KRT6C | NM_058242 | 6 Kb | 2223 bp | 9 | 286887 | |
| KRT7 | NM_005556 | 15.76 Kb | 1702 bp | | 3855 | |
| KRT71 | | 9.2 Kb | 2255 bp | 9 | | |
| KRT72 | | 15.9 Kb | 1985 bp | 9 | | |
| KRT73 | | 11 Kb | 2323 bp | 9 | | |
| KRT74 | | 8 Kb | 2799 bp | 9 | | |
| KRT75 | | 10.2 Kb | 2125 bp | 9 | | |
| KRT76 | | 9.1 Kb | 2513 bp | 9 | | |
| KRT78 | | 10.03 Kb | 1785 bp | 9 | | |
| KRT79 | | 12.85 Kb | 2144 bp | 9 | | |
| KRT8 | NM_002273 | 7.85 Kb | 1746 bp | 8 | 3856 | |
| KRT80 | | 16.2 Kb | 3411 bp | 7 | | |
| KRT81 | | 5.6 Kb | 1925 bp | 9 | | |
| KRT82 | | 12.44 Kb | 2681 bp | 9 | | |
| KRT83 | | 7.09 Kb | 1883 bp | 9 | | |
| KRT84 | | 7.8 Kb | 2404 bp | 9 | | |
| KRT85 | | 7.52 Kb | 2508 bp | 9 | | |
| KRT86 | | 6.6 Kb | 2108 bp | 9 | | |
| KRT9 | NM_000226 | 6.21 Kb | 2287 bp | 8 | 3857 | epidermolytic palmoplantar keratoderma |

TABLE 2

Basis for constructs derived from collagens

| Gen | Exons | Gene ID |
|---|---|---|
| COL1A1 | 51 | 1277 |
| COL2A1 | 54 | 1280 |
| COL3A1 | 51 | 1281 |
| COL4A1 | 45 | 1282 |
| COL5A1 | 67 | 1289 |
| COL6A1 | 35 | 1291 |
| COL7A1 | 118 | 1294 |
| COL8A1 | 5 | 1295 |
| COL9A1 | 38 | 1297 |
| COL10A1 | 3 | 1300 |
| COL11A1 | 66 | 1301 |
| COL12A1 | 66 | 1303 |
| COL13A1 | 39 | 1305 |
| COL14A1 | 46 | 7373 |
| COL15A1 | 42 | 1306 |
| COL16A1 | 71 | 1307 |
| COL17A1 | 56 | 1308 |
| COL18A1 | 42 | 80781 |
| COL19A1 | 51 | 1310 |
| COL20A1 | 37 | 57642 |
| COL21A1 | 29 | 81578 |
| COL22A1 | 65 | 169044 |
| COL23A1 | 29 | 91522 |
| COL24A1 | 60 | 255631 |
| COL25A1 | 38 | 84570 |
| COL26A1 | 14 | 136227 |
| COL27A1 | 61 | 85301 |
| COL28A1 | 35 | 340267 |
| COL29A1 | 10 | 256076 |

TABLE 3

Basis for constructs derived from tumour necrosis factor-alpha

| | Exons | GeneID | GeneBankID |
|---|---|---|---|
| TNF-a | 4 | 7124 | NM_000594 |

TABLE 4

Basis for constructs derived from interleukins

| Interleukin | Exons | GeneID | GeneBankID |
|---|---|---|---|
| 1alpha | 7 | 3552 | NM_000575 |
| 1beta | 7 | 3553 | NM_000576 |
| 1F5 | 5 | 26525 | NM_173170 |
| 1F6 | 3 | 27179 | NM_014440 |
| 1F7 | 5 | 27178 | NM_014439 |
| 1F8 | 6 | 27177 | NM_014438 |
| 1F9 | 5 | 56300 | NM_019618 |
| 1F10 | 5 | 84639 | NM_173161 |
| 2 | 4 | 3558 | NM_000586 |
| 3 | 5 | 3562 | NM_000588 |
| 4 | 4 | 3565 | NM_000589 |
| 5 | 4 | 3567 | NM_000879 |
| 6 | 5 | 3569 | NM_000600 |
| 7 | 6 | 3574 | NM_000880 |
| 8 | 4 | 3576 | NM_000584 |
| 9 | 5 | 3578 | NM_000590 |
| 10 | 5 | 3586 | NM_000572 |
| 11 | 5 | 3589 | NM_000641 |
| 12a | 7 | 3592 | NM_000882 |
| 12b | 8 | 3593 | NM_002187 |
| 13 | 4 | 3596 | NM_002188 |
| 15 | 6 | 3600 | NM_000585 |

TABLE 4-continued

Basis for constructs derived from interleukins

| Interleukin | Exons | GeneID | GeneBankID | |
|---|---|---|---|---|
| 16 | 21 | 3603 | NM_172217 | |
| 17a | 3 | 3605 | NM_002190 | |
| 17b | 3 | 27190 | NM_014443 | |
| 17c | 3 | 27189 | NM_013278 | |
| 17d | 3 | 53342 | NM_138284 | |
| 17f | 3 | 112744 | NM_052872 | |
| 18 | 6 | 3606 | NM_001562 | |
| 19 | 6 | 29949 | NM_153758 | |
| 20 | 5 | 50604 | NM_018724 | |
| 21 | 5 | 59067 | NM_021803 | |
| 22 | 6 | 50616 | NM_020525 | |
| 23A | 4 | 51561 | NM_016584 | |
| 24 | 7 | 11009 | NM_006850 | |
| 25 | 2 | 64806 | NM_022789 | |
| 26 | 5 | 55801 | NM_018402 | |
| 27 (30) | 5 | 246778 | NM_145659 | |
| 28a | 6 | 282616 | NM_172138 | |
| 28b | 5 | 282617 | NM_172139 | |
| 29 | 5 | 282618 | NM_172140 | |
| 31 | 3 | 386653 | NM_001014336 | |
| 32 | 6 | 9235 | NM_004221 | |
| 33 | 7 | 90865 | NM_033439 | |
| 34 | 6 | 146433 | NM_152456 | |

TABLE 5

Basis for constructs derived from ICAM/VCAM

| | Exons | GeneID | GeneBankID | |
|---|---|---|---|---|
| ICAM | | | | |
| 1 | 7 | 3383 | NM_000201 | |
| 2 | 4 | 3384 | NM_001099786 | transcript variant 1 |
| | | | NM_001099787 | transcript variant 2 |
| | | | NM_001099788 | transcript variant 3 |
| | | | NM_001099789 | transcript variant 4 |
| | | | NM_000873 | transcript variant 5 |
| 3 | 7 | 3385 | NM_002162 | |
| 4 | 3 | 3386 | NM_001544 | transcript variant 1 |
| | | | NM_022377 | transcript variant 2 |
| | | | NM_001039132 | transcript variant 3 |
| 5 | 11 | 7087 | NM_003259 | |
| VCAM | | | | |
| 1 | 9 | 7412 | NM_001078 | transcript variant 1 |
| | 8 | | NM_080682 | transcript variant 2 |

TABLE 6

Basis for constructs derived from kallikreins

| Kallikrein | Exons | GeneID | GeneBankID |
|---|---|---|---|
| KLK1 | 5 | 3816 | NM_002257 |
| KLK2 | 5 | 3817 | NM_005551.3 |
| KLK3 | 5 | 354 | NM_145864 |
| KLK4 | 6 | 9622 | NM_004917 |
| KLK5 | 6 | 25818 | NM_012427 |
| KLK6 | 5 | 5653 | NM_002774 |
| KLK7 | 6 | 5650 | NM_005046 |
| KLK8 | 6 | 11202 | NM_007196 |
| KLK9 | 5 | 284366 | NM_012315 |
| KLK10 | 6 | 5655 | NM_002776 |
| KLK12 (transcript variant 1) | 7 | 43849 | NM_019598 |
| KLK12 (transcript variant 2) | 6 | | NM_145894 |

TABLE 6-continued

Basis for constructs derived from kallikreins

| Kallikrein | Exons | GeneID | GeneBankID |
|---|---|---|---|
| KLK12 (transcript variant 3) | 5 | | NM_145895 |
| KLK11 | 6 | 11012 | NM_006853 |
| KLK13 | 5 | 26085 | NM_015596 |
| KLK14 | 8 | 43847 | NM_022046 |
| KLK15 | 5 | 55554 | NM_017509 |

TABLE 7

Basis for constructs derived from Matrix Metalloproteinases

| Matrix Metalloproteinase | Exons | GeneID | GeneBankID |
|---|---|---|---|
| MMP1 | 10 | 4312 | NM_002421 |
| MMP2 | 13 | 4313 | NM_004530 |
| MMP3 | 10 | 4314 | NM_002422 |
| MMP7 | 6 | 4316 | NM_002423 |
| MMP8 | 10 | 4317 | NM_002424 |
| MMP9 | 13 | 4318 | NM_004994 |
| MMP10 | 10 | 4319 | NM_002425 |
| MMP11 | 8 | 4320 | NM_005940 |
| MMP12 | 10 | 4321 | NM_002426 |
| MMP13 | 10 | 4322 | NM_002427 |
| MMP14 | 10 | 4323 | NM_004995 |
| MMP15 | 10 | 4324 | NM_002428 |
| MMP16 | 10 | 4325 | NM_005941 |
| MMP17 | 10 | 4326 | NM_016155 |
| MMP19 | 9 | 4327 | NM_002429 |
| MMP20 | 10 | 9313 | NM_004771 |
| MMP21/MMP23A | 7 | 118856 | NM_147191 |
| MMP23b (ex MMP22) | 7 | 8510 | NM_006983 |
| MMP24 | 9 | 10893 | NM_006690 |
| MMP25 | 10 | 64386 | NM_022468 |
| MMP26 | 7 | 56547 | NM_021801 |
| MMP27 | 10 | 64066 | NM_022122 |
| MMP28 | 9 | 79148 | NM_001032278 |

TABLE 8

Basis for constructs derived from laminins

| Laminin | Exons | GeneID | GeneBankID |
|---|---|---|---|
| LAMA1 | 63 | 284217 | NM_005559 |
| LAMA2 | 64 | 3908 | NM_000426 |
| LAMA3 | 38 | 3909 | NM_000227 |
| | | | NM_198129 |
| LAMA4 | 39 | 3910 | NM_001105209 |
| LAMA5 | 80 | 3911 | NM_005560 |
| LAMB1 | 34 | 3912 | NM_002291 |
| LAMB2 | 32 | 3913 | NM_002292 |
| LAMB3 | 23 | 3914 | NM_000228 |
| LAMB4 | 34 | 22798 | XM_209857 |
| LAMC1 | 28 | 3915 | NM_002293 |
| LAMC2 | 23 | 3918 | NM_005562 |
| LAMC3 | 28 | 10319 | NM_006059 |

TABLE 9

Basis for constructs derived from CFTR

| | Exons | GeneID | GeneBankID |
|---|---|---|---|
| CFTR | 27 | 1080 | NM_000492 |

TABLE 10

Basis for constructs derived from Integrins

| Integrins | Exons | GeneID | GeneBankID | |
|---|---|---|---|---|
| a1 | 29 | 3672 | NM_181501 | |
| a2 | 30 | 3673 | NM_002203 | |
| a2b | 30 | 3674 | NM_000419 | |
| a3 | 26 | 3675 | NM_002204 | transcript variant a |
|   |   |   | NM_005501 | transcript variant b |
| a4 | 28 | 3676 | NM_000885 | |
| a5 | 30 | 3678 | NM_002205 | |
| a6 | 26 | 3655 | NM_001079818 | transcript variant 1 |
|   |   |   | NM_000210 | transcript variant 2 |
| a7 | 25 | 3679 | NM_002206 | |
| a8 | 30 | 8516 | NM_003638 | |
| a9 | 28 | 3680 | NM_002207 | |
| a10 | 30 | 8515 | NM_003637 | |
| a11 | 31 | 22801 | NM_012211 | |
| ad | 30 | 3681 | NM_005353 | |
| ae | 31 | 3682 | NM_002208 | |
| al | 31 | 3683 | NM_002209 | |
| am | 30 | 3684 | NM_000632 | |
| av | 30 | 3685 | NM_002210 | |
| aw | ? | 3686 | ? | |
| ax | 30 | 3687 | NM_000887 | |
| β1 | 23 | 3688 | NM_002211 | transcript variant 1A |
|   |   |   | NM_033666 | transcript variant 1B |
|   |   |   | NM_033667 | transcript variant 1C-1 |
|   |   |   | NM_033669 | transcript variant 1C-2 |
|   |   |   | NM_033668 | transcript variant 1D |
|   |   |   | NM_133376 | transcript variant 1E |
| β2 | 16 | 3689 | NM_000211 | |
| β3 | 15 | 3690 | NM_000212 | |
| β4 | 42 |   | NM_000213 | transcript variant 1 |
|   |   |   | NM_001005619 | transcript variant 2 |
|   |   |   | NM_001005731 | transcript variant 3 |
| β5 | 17 | 3693 | NM_002213 | |
| β6 | 15 | 3694 | NM_000888 | |
| β7 | 16 | 3695 | NM_000889 | |
| β8 | 14 | 3696 | NM_002214 | |

TABLE 11

Basis for constructs derived from plectin

| Plectin | Exons | GeneID | |
|---|---|---|---|
|   | 33 | NM_000445 | Isoform 1 |
|   | 33 | NM_201378 | Isoform 2 |
|   | 33 | NM_201379 | Isoform 3 |
|   | 33 | NM_201380 | Isoform 6 |
|   | 33 | NM_201381 | Isoform 7 |
|   | 33 | NM_201382 | Isoform 8 |
|   | 33 | NM_201383 | Isoform 10 |
|   | 33 | NM_201384 | Isoform 11 |

In the present invention, the term "homologous" refers to the degree of identity between sequences of two nucleic acid sequences. The homology of homologous sequences is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm (Nucleic Acid Res., 22(22): 4673 4680 (1994). Commonly available sequence analysis software, more specifically, Vector NTI, GENETYX, BLAST or analysis tools provided by public databases, such as found on, e.g., http://dragon.bio.purdue.edu/bioinfolinks/ may also be used.

The present invention therefore generally encompasses RTMs according to the present invention, wherein the RTMs comprise any combination of coding domain comprising exons x to y for the respective gene as given in the above tables, where x is an integer selected from 1 or 2 to the maximal number of exons, and y is an integer selected from 0 and x+1, wherein x+1 is limited by the maximal number of exons of said gene.

As preferred examples, an RTM derived from MMP9 (NM_004994, see table 7) can comprise a coding domain comprising of the exons 1 to 13, or between 2 and 13 exons of the gene (with x+1 being limited by the 13 exons of MMP9); an RTM derived from plectin (NM_000445, see table 11) can comprise a coding domain comprising one or more of the exons 1 to 33, or between 2 and 33 exons of the gene (with x+1 being limited by the 10 exons of plectin, isoform 1); an RTM derived from keratin 14 (NM_000526, see table 1) can comprise a coding domain comprising one or more of the exons 1 to 8, or between 2 and 8 exons of the gene (with x+1 being limited by the 8 exons of keratin 14); an RTM derived from collagen type 7 (Gene ID 1294, see table 2) can comprise a coding domain comprising one or more of the exons 1 to 118, or between 2 and 118 exons of the gene (with x+1 being limited by the 118 exons of collagen type 7); and an RTM derived from ICAM-1 (NM_000201, see table 5) can comprise a coding domain comprising one or more of the exons 1 to 7, or between 2 and 7 exons of the gene (with x+1 being limited by the 7 exons of ICAM-1). As further examples, for 5' trans-splicing, the front of the gene is replaced, so the RTMs can deliver only exon 1, exons 1 and 2, 1 to 3, 1 to 4, etc. For plectin, exon 1 is left out, so in this case the construct is 2, 2 and 3, 2 to 4, etc. In the case of 3' trans-splicing only the terminal exon y can be replaced, leading to y+(y−1), y to (y−2), y to (y−3), etc. Double trans-splicing RTMs can replace any internal exon or combinations of exons.

In one preferred embodiment of the RTMs according to the present invention, said RTM comprises at least one intron and/or exon, preferably exon, derived from other genes, in order to provide additional desired functionalities. Preferred examples are the introduction of a binding domain complementary to intron 1 of ICAM-1 fused to interleukin-10, or a construct comprising a RTM to bind in the MMP-9 gene, into which HSV-thymidine-kinase is introduced. After the addition of e.g. gancyclovir, this is phosphorylated and becomes activated. In other preferred embodiments, the exon comprises naturally occurring or artificially introduced stop-codons in order to reduce gene expression or contains other sequences which produce an RNAi-like effect.

The RTM according to the present invention, wherein said gene is selected from the group of plectin, keratin 14, collagen type 7, keratin 5, keratin 6, collagen type 17, laminin A3, laminin B3, g2, integrin β4, a6, CFTR, and interleukin-10 (IL-10), preferably at least one of plectin, keratin 14, collagen 7A1, collagen 17A1 and IL-10. Mutations in these genes have been linked with diseases of skin cells as described herein, and related diseases. IL-10 is an immuno-suppressive interleukin that can be used to treat autoimmune diseases.

Further preferred is an RTM according to the present invention, wherein said nucleic acid molecule further comprises at least one safety sequence in said splicing domain. Said "safety" is incorporated into the spacer, binding domain, or elsewhere in the RTM to prevent non-specific trans-splicing. This is a region of the RTM that covers elements of the 3' and/or 5' splice site of the RTM by relatively weak complementarity, preventing non-specific trans-splicing. The RTM is designed in such a way that upon hybridization of the binding/targeting portion(s) of the RTM, the 3' and/or 5' splice site is uncovered and becomes fully active. Such "safety" sequences comprises one or more complementary stretches of cis-sequence (or could be a second, separate, strand of nucleic acid) which binds to one or both sides of the RTM branch point, pyrimidine tract, 3' splice site and/or 5' splice site (splicing elements), or could bind to parts of the splicing elements themselves. This "safety" binding prevents the splicing elements from being active (i.e. block U2 snRNP or other splicing factors from attaching to the RTM splice site or recognition elements). The binding of the "safety" may be disrupted by the binding of the target binding region of the RTM to the target pre-mRNA, thus exposing and activating the RTM splicing elements (making them available to trans-splice into the target pre-mRNA).

Further preferred is an RTM according to the present invention, wherein the binding of the nucleic acid molecule to the target pre-mRNA is mediated by complementarity (i.e. based on base-pairing characteristics of nucleic acids), triple helix formation (as described in, for example, Suzuki T. Targeted gene modification by oligonucleotides and small DNA fragments in eukaryotes. Front Biosci. 2008 Jan. 1; 13:737-44. Review. Dang N, Klingberg S, Marr P, Murrell D F. Review of collagen VII sequence variants found in Australasian patients with dystrophic epidermolysis bullosa reveals nine novel COL7A1 variants. J Dermatol Sci. 2007 June; 46(3):169-78. Review), or protein-nucleic acid interaction (as described in the respective literature).

Another aspect of the present invention relates to an RTM according to the present invention, wherein the exon to be trans-spliced comprises naturally occurring or artificially introduced stop-codons and/or a stem-forming structure in order to provide an RNAi-like effect.

Another aspect of the present invention relates to an RTM according to the present invention, where the RTMs has 3'UTR sequences or ribozyme sequences added to the 3 or 5' end.

The compositions of the invention in one preferred embodiment include RTM molecules designed to interact with a natural target pre-mRNA molecule (hereinafter referred to as "pre-mRNA") and mediate a trans-splicing reaction resulting in the generation of a novel chimeric RNA molecule (hereinafter referred to as "pre-miRNA") capable of reducing expression of the target mRNA. The methods of the invention encompass contacting the RTMs of the invention with a natural target pre-mRNA under conditions in which a portion of the RTM is spliced to the natural pre-mRNA to form a novel pre-miRNA. The RTMs of the invention are genetically engineered so that the novel pre-miRNA resulting from the trans-splicing reaction is capable of being further processed to form an active miRNA having interfering activity for a specific mRNA. The specific target mRNA may be the mRNA normally resulting from cis-splicing of the target pre-mRNA, or alternatively, may be an unrelated mRNA. Generally, the target pre-mRNA is chosen because it is expressed within a specific cell type thereby providing a means for targeting expression of the novel RNA to a selected cell type. Such targeted expression of the pre-miRNA can be used to reduce the expression of the target pre-mRNA in diseases/pathologies associated with expression of the target mRNA.

Further preferred is an RTM according to the present invention that is a DNA, RNA or DNA/RNA hybrid molecule. Thus, in a further aspect thereof, the present invention is directed at a nucleic acid, which comprises at least one nucleic acid encoding one of the RTMs of the present invention. Preferably the nucleic acid consists of DNA, RNA or DNA/RNA hybrid molecules, wherein the DNA or RNA preferentially is either single or double stranded. Also comprised are RNAs or DNAs, which hybridize to one of the aforementioned RNAs or DNAs preferably under stringent conditions like, for example, hybridization at 60° C. in 2.5× SSC buffer and several washes at 37° C. at a lower buffer concentration like, for example, 0.5×SSC buffer and which encode proteins exhibiting lipid phosphate phosphatase activity and/or association with plasma membranes. Additional reagents required for carrying out stringent Northern or Southern blots like, for example, single stranded salmon sperm DNA are well known in the art. Also comprised are nucleic acid sequences, which are related to the nucleic acids according to the present invention and/or the hybridizing nucleic acids as outlined above by the degeneration of the genetic code.

In some instances it might be desirable to interfere with, for example, the transcription or translation of the nucleic acids of the present invention and, therefore, the present invention is also directed at a nucleic acid, which is complementary to the nucleic acid of the present invention and, thus, is capable of inhibiting, for example, transcription or translation. A preferred embodiment of such a complementary nucleic acid is a so called anti-sense oligonucleotide (R. Q. Zheng and D. M. Kemeny (1995) Clin. Exp. Immunol. 100:380-2, W. Nellen and C. Lichtenstein (1993) Trends. Biochem. Sci. 18:419-423 and C. A. Stein (1992) Leukemia 6:967-74), ribozymes (M. Amarzguioui and H. Prydz (1998) Cell. Mol. Life Sci. 54:1175-1202, N. K. Vaish et al (1998) Nucleic Acids Res. 96:5237-5242, Persidis (1997) Nat. Biotechnol. 15:921-922 and L. A. Couture and D. T. Stinchcomb (1996) Trends Genet. 12:510-515) and/or so called small interfering RNA-molecules (siRNAs) (S. M. Elbashir et al. (2001) Nature 411:494-498). Anti-sense oligonucleotides have in a preferred embodiment a length of at least 20, preferable of at least about 30, more preferably of at least about 40 and most preferably a length of at least about 50 nucleic acids.

Oligonucleotides are generally rapidly degraded by endo- or exonucleases, which are present in the cell, in particular by DNases and RNases and, therefore, it is advantageous to modify the nucleic acids which are used, for example, in anti-sense strategies, as ribozymes or siRNAs to stabilize them against degradation and thereby prolong the time over which an effective amount of the nucleic acid is maintained within the cell (L. Beigelmann et al. (1995) Nucleic acids Res. 23:3989-94, WO 95/11910, WO 98/37340 and WO 97/29116). Typically such stabilization can be obtained by the introduction of one or more internucleotide phosphate groups and/or by the introduction of one or more non-phosphor-internucleotides.

Suitable modified internucleotides are summarized in, for example, Uhlmann and Peimann (1990) Can. Rev. 90:544. Modified internucleotide phosphate residues and/or non-phosphate bridges which can be used in a nucleic acid of the invention comprise, for example, methylphosphonate, phosphorthioate, phosphoramidate, phosphordithionate, phosphate ester, non-phosphor internucleotide analogues, which can be used in nucleic acids of the invention include, for example, siloxane bridges, carbonate bridges, carboxymethylester, acetamid bridges and/or thioether bridges.

In a preferred embodiment of the invention, splicing enhancers such as, for example, sequences referred to as exonic splicing enhancers may also be included in the structure of the synthetic RTMs. Transacting splicing factors, namely the serine/arginine-rich (SR) proteins, have been shown to interact with such exonic splicing enhancers and modulate splicing (See, Tacke et al., 1999, Curr. Opin. Cell Biol. 11:358-362; Tian et al., 2001, J. Biological Chemistry 276:33833-33839; Fu, 1995, RNA 1:663-680). The RTM thus preferably includes one or more complementary sequences to intron and/or exon sequences in the target pre-mRNA. This binds the RTM to the chosen endogenous target pre-mRNA, so that the RTM splice site is more likely to complete a splicing reaction with a splice site in the target pre-mRNA.

Additional features can be added to the RTM molecule, such as polyadenylation signals to modify RNA expression/stability, or 5' splice sequences to enhance splicing, additional binding regions, "safety"-self complementary regions, additional splice sites, or protective groups to modulate the stability of the molecule and prevent degradation. In addition, stop codons may be included in the RTM structure to prevent translation of unspliced RTMs. Further elements such as a 3' hairpin structure, circularized RNA, nucleotide base modification, or synthetic analogs can be incorporated into RTMs to promote or facilitate nuclear localization and spliceosomal incorporation, and intra-cellular stability.

When specific RTMs are to be synthesized in vitro (synthetic RTMs), such RTMs can be modified at the base moiety, sugar moiety, or phosphate backbone, for example, to improve stability of the molecule, hybridization to the target mRNA, transport into the cell, etc. For example, modification of a RTM to reduce the overall charge can enhance the cellular uptake of the molecule. In addition modifications can be made to reduce susceptibility to nuclease or chemical degradation. The nucleic acid molecules may be synthesized in such a way as to be conjugated to another molecule such as a peptides (e.g., for targeting host cell receptors in vivo), or an agent facilitating transport across the cell membrane (see, e.g., Letsinger et al., 1989, Proc. Natl. Acad. Sci. USA 86: 6553-6556; Lemaitre et al., 1987, Proc. Natl. Acad. Sci. 84:648-652; PCT Publication No. WO 88/09810, published Dec. 15, 1988) or the blood-brain barrier (see, e.g., PCT Publication No. WO 89/10134, published Apr. 25, 1988), hybridization-triggered cleavage agents (see, e.g., Krol et al., 1988, BioTechniques 6: 958-976) or intercalating agents (see, e.g., Zon, 1988, Pharm. Res. 5: 539-549). To this end, the nucleic acid molecules may be conjugated to another molecule, e.g., a peptide, hybridization triggered cross-linking agent, transport agent, hybridization-triggered cleavage agent, etc.

Various other well-known modifications to the nucleic acid molecules can be introduced as a means of increasing intracellular stability and half-life (see also above for oligonucleotides). Possible modifications include, but are not limited to, the addition of flanking sequences of ribonucleotides to the 5' and/or 3' ends of the molecule. In some circumstances where increased stability is desired, nucleic acids having modified internucleoside linkages such as 2'-O-methylation may be preferred. Nucleic acids containing modified internucleoside linkages may be synthesized using reagents and methods that are well known in the art (see, Uhlmann et al., 1990, Chem. Rev. 90: 543-584; Schneider et al., 1990, Tetrahedron Lett. 31:335 and references cited therein).

When synthetically produced, the synthetic RTMs of the present invention are preferably modified in such a way as to increase their stability in the cells. Since RNA molecules are sensitive to cleavage by cellular ribonucleases, it may be preferable to use as the competitive inhibitor a chemically modified oligonucleotide (or combination of oligonucleotides) that mimics the action of the RNA binding sequence but is less sensitive to nuclease cleavage. In addition, the synthetic RTMs can be produced as nuclease resistant circular molecules with enhanced stability to prevent degradation by nucleases (Puttaraju et al., 1995, Nucleic Acids Symposium Series No. 33: 49-51; Puttaraju et al., 1993, Nucleic Acid Research 21: 4253-4258). Other modifications may also be required, for example to enhance binding, to enhance cellular uptake, to improve pharmacology or pharmacokinetics or to improve other pharmaceutically desirable characteristics.

Modifications, which may be made to the structure of the synthetic RTMs include but are not limited to backbone modifications such as use of: (i) phosphorothioates (X or Y or W or Z=S or any combination of two or more with the remainder as O). e.g. Y=S (Stein, C. A., et al., 1988, Nucleic Acids Res., 16:3209-3221), X=S (Cosstick, R., et al., 1989, Tetrahedron Letters, 30, 4693-4696), Y and Z=S (Brill, W. K.-D., et al., 1989, J. Amer. Chem. Soc., 111: 2321-2322); (ii) methylphosphonates (e.g. Z=methyl (Miller, P. S., et al., 1980, J. Biol. Chem., 255: 9659-9665); (iii) phosphoramidates ($Z=N-(alkyl)_2$ e.g. alkyl methyl, ethyl, butyl) (Z=morpholine or piperazine) (Agrawal, S., et al., 1988, Proc. Natl. Acad. Sci. USA 85: 7079-7083) (X or W=NH) (Mag, M., et al., 1988, Nucleic Acids Res., 16:3525-3543); (iv) phosphotriesters (Z=O-alkyl e.g. methyl, ethyl, etc) (Miller, P. S., et al., 1982, Biochemistry, 21: 5468-5474); and (v) phosphorus-free linkages (e.g. carbamate, acetamidate, acetate) (Gait, M. J., et al., 1974, J. Chem. Soc. Perkin 1, 1684-1686; Gait, M. J., et al., 1979, J. Chem. Soc. Perkin 1, 1389-1394).

In addition, sugar modifications may be incorporated into the RTMs of the invention. Such modifications include the use of: (i) 2'-ribonucleosides (R=H); (ii) 2'-O-methylated nucleosides (R=OMe) (Sproat, B. S., et al., 1989, Nucleic Acids Res., 17:3373-3386); and (iii) 2'-fluoro-2'-riboxynucleosides (R=F) (Krug, A., et al., 1989, Nucleosides and Nucleotides, 8: 1473-1483).

Further, base modifications that may be made to the RTMs, including but not limited to use of: (i) pyrimidine derivatives substituted in the 5-position (e.g. methyl, bromo, fluoro etc) or replacing a carbonyl group by an amino group (Piccirilli, J. A., et al., 1990, Nature, 343:33-37); (ii) purine derivatives lacking specific nitrogen atoms (e.g. 7-deaza adenine, hypoxanthine) or functionalized in the 8-position (e.g. 8-azido adenine, 8-bromo adenine) (for a review see Jones, A. S., 1979, Int. J. Biolog. Macromolecules, 1: 194-207).

In addition, the RTMs may be covalently linked to reactive functional groups, such as: (i) psoralens (Miller, P. S., et al., 1988, Nucleic Acids Res., Special Pub. No. 20, 113-114), phenanthrolines (Sun, J-S., et al., 1988, Biochemistry, 27: 6039-6045), mustards (Vlassov, V. V., et al, 1988, Gene, 72:313-322) (irreversible cross-linking agents with or without the need for co-reagents); (ii) acridine (intercalating agents) (Helene, C., et al., 1985, Biochimie, 67: 777-783); (iii) thiol derivatives (reversible disulphide formation with proteins) (Connolly, B. A., and Newman, P. C., 1989, Nucleic Acids Res., 17: 4957-4974); (iv) aldehydes (Schiffs base formation); (v) azido, bromo groups (UV cross-linking); or (vi) ellipticines (photolytic cross-linking) (Perrouault, L., et al., 1990, Nature, 344: 358-360).

In an embodiment of the invention, oligonucleotide mimetics in which the sugar and internucleoside linkage, i.e., the backbone of the nucleotide units, are replaced with novel groups can be used. For example, one such oligonucleotide mimetic which has been shown to bind with a higher affinity to DNA and RNA than natural oligonucleotides is referred to as a peptide nucleic acid (PNA) (for a review see, Uhlmann, E. 1998, Biol. Chem. 379: 1045-52). Thus, PNA may be incorporated into synthetic RTMs to increase their stability and/or binding affinity for the target pre-mRNA.

In another embodiment of the invention synthetic RTMs may covalently linked to lipophilic groups or other reagents capable of improving uptake by cells. For example, the RTM molecules may be covalently linked to: (i) cholesterol (Letsinger, R. L., et al, 1989, Proc. Natl. Acad. Sci. USA, 86: 6553-6556); (ii) polyamines (Lemaitre, M., et al., 1987, Proc. Natl. Acad. Sci, USA, 84: 648-652); other soluble polymers (e.g. polyethylene glycol) to improve the efficienty with which the RTMs are delivered to a cell. In addition, combinations of the above identified modifications may be utilized to increase the stability and delivery of RTMs into the target cell. The RTMs of the invention can be used in methods designed to produce a novel chimeric RNA in a target cell.

Another aspect of the present invention then relates to a recombinant expression vector, comprising a RTM according to the present invention as above. A vector within the meaning of the present invention is a nucleic acid which is capable of being introduced or of introducing nucleic acid as comprised into a cell. It is preferred that the RTMs encoded by the introduced nucleic acid are expressed within the cell upon introduction of the vector. Preferably, said vector is a eukaryotic expression vector, preferably a vector comprising virus derived sequences. Further preferred is a vector of the present invention, wherein said vector furthermore comprises skin-cell and preferably keratinocyte specific regulatory elements in order to direct transgene expression.

Suitable expression vectors for in vitro or in vivo expression can be found in the literature. These vectors can also be easily modified by the person of skill in the art in order to be applied in the methods of the present invention. The expression vectors usually contain all genetic elements that are necessary for the production of a specific RTM molecule. In some embodiments of the present invention, the expression vectors according to the present invention can have the form of a "transgene", i.e. an expression element in, for example, a suitable vector that is designed for an expression and particularly an inducible and/or controllable expression in vivo. Accordingly, the transgene comprises nucleic acids of the present invention together with certain genetic control elements for the expression as discussed herein.

In a preferred embodiment the vector of the present invention comprises plasmids, phagemids, phages, cosmids, artificial mammalian chromosomes, knock-out or knock-in constructs, viruses, in particular adenovirus, vaccinia virus, lentivirus (Chang, L. J. and Gay, E. E. (20001) Curr. Gene Therap. 1: 237-251), Herpes simplex virus (HSV-1, Carlezon, W. A. et al. (2000) Crit. Rev. Neurobiol.; 14(1): 47-67), baculovirus, retrovirus, adeno-associated-virus (AAV, Carter, P. J. and Samulski, R. J. (2000) J. Mol. Med. 6: 17-27), rhinovirus, human immune deficiency virus (HIV), filovirus and engineered versions thereof (see, for example, Cobinger G. P. et al (2001) Nat. Biotechnol. 19: 225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3: 466-76 and Springer et al. (1998) Mol. Cell. 2: 549-58). Liposomes are usually small unilamellar or multilamellar vesicles made of neutral cationic and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, cholesterol, phospholipide like, for example, phosphatidylcholin (PC), phosphatidylserin (PS) and the like, DOTMA (1,2-Dioleyloxpropyl-3-trimethylammoniumbromid) and DPOE (Dioleoylphosphatidylethanolamin) which both have been used on a variety of cell lines. Nucleic acid coated particles are another means for the introduction of nucleic acids into cells using so called "gene guns", which allow the mechanical introduction of particles into the cells. Preferably the particles are themselves inert, and therefore, are in a preferred embodiment made out of gold spheres.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs ((1978) Nature 275, 104-109) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Another aspect of the present invention then relates to a recombinant skin cell, preferably a recombinant keratinocyte, fibroblast or endothelial cell, comprising a RTM-molecule according to the present invention, and/or a recombinant expression vector according to the present invention. In addition to the description above regarding recombinant expression vectors, the nucleic acid molecule encoding the RTM can be introduced into the skin cell, preferably a keratinocyte, fibroblast or endothelial cell by any means available in the art. In a presently preferred embodiment, a retroviral vector is used to transduce the keratinocytes in vitro. More particularly, the pBabe puro retroviral vector of Morganstern and Land (1990) can be used, and the DNA encoding the RTM be inserted. Transduction of the preferred keratinocytes using the BABE vector is described in the literature. The exact method of introducing the altered nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors. Physical transduction techniques can also be used, such as liposome delivery and receptor-mediated and other endocytosis mechanisms. This invention can be used in conjunction with any of these or other commonly used gene transfer methods.

Other methods known in the art can also be used to introduce the nucleic acid encoding the RTMs into skin cells, such as keratinocytes, fibroblast or endothelial cell as already described also above. One method is microinjection, in which DNA is injected directly into the cytoplasm of cells through fine glass needles. Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Another aspect of the present invention then relates to a pharmaceutical preparation, comprising a physiologically acceptable carrier and the RTM-molecule according to the present invention, the recombinant expression vector according to the present invention, or the recombinant skin cell according to the present invention. Yet another aspect of the present invention then relates to an RTM-molecule according to the present invention, the recombinant expression vector according to the present invention, the recombinant skin cell according to the present invention, or the pharmaceutical preparation according to the present invention for use as a medicament.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the synthetic is administered. Examples of suitable pharmaceutical carriers are described in "Remington's Pharmaceutical sciences" by E. W. Martin.

In specific embodiments, pharmaceutical compositions are administered: (1) in diseases or disorders involving an absence or decreased (relative to normal or desired) level of an endogenous protein or function, for example, in hosts where the protein is lacking, genetically defective, biologically inactive or underactive, or under expressed; or (2) in diseases or disorders wherein, in vitro or in vivo, assays indicate the utility of synthetic RTMs that inhibit the function of a particular protein. The activity of the protein encoded for by the chimeric mRNA resulting from the synthetic RTM mediated trans-splicing reaction can be readily detected, e.g., by obtaining a host tissue sample (e.g., from biopsy tissue) and assaying it in vitro for mRNA or protein levels, structure and/or activity of the expressed chimeric mRNA. Many methods standard in the art can be thus employed, including but not limited to immunoassays to detect and/or visualize the protein encoded for by the chimeric mRNA (e.g., Western blot, immuno-precipitation followed by sodium dodecyl sulfate polyacrylamide gel electrophoresis, immunocytochemistry, etc.) and/or hybridization assays to detect formation of chimeric mRNA expression by detecting and/or visualizing the presence of chimeric mRNA (e.g., Northern assays, dot blots, in situ hybridization, and Reverse-Transcription PCR, etc.), etc. Alternatively, direct visualization of a reporter gene either encoded by the synthetic RTM or associated with a RTM may be carried out.

The present invention also provides for pharmaceutical compositions comprising an effective amount of a synthetic RTM or a nucleic acid encoding a synthetic RTM, and a pharmaceutically acceptable carrier. In a specific embodiment, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Other control release drug delivery systems, such as nanoparticles, matrices such as controlled-release polymers, hydrogels. The RTM or synthetic RTM will be administered in amounts which are effective to produce the desired effect in the targeted cell. Effective dosages of the synthetic RTMs can be determined through procedures well known to those in the art which address such parameters as biological half-life, bioavailability and toxicity. The amount of the composition of the invention which will be effective will depend on the nature of the disease or disorder being treated, and can be determined by standard clinical techniques. In addition, in vitro assays may optionally be employed to help identify optimal dosage ranges.

The present invention also provides a pharmaceutical pack or kit comprising one or more containers filled with one or more of the ingredients of the pharmaceutical compositions of the invention optionally associated with such container (s) can be a notice in the form prescribed by a governmental agency regulating the manufacture, use or sale of pharmaceuticals or biological products, which notice reflects approval by the agency of manufacture, use or sale for human administration.

Any molecule of the invention, nucleic acid, expression vector, or cell is useful for the treatment of the disorders as described herein. Therefore any molecule of the present invention may be used as medicament or in the manufacture of a medicament. The molecule may be used by itself or combined with other molecule(s) of the invention or (a) known molecule(s).

Preferably, the medicament of the present invention can be administered directly into the patient, into the affected organ or systemically i.d., i.m., s.c., i.p. and i.v., or applied ex vivo to cells derived from the patient or a human cell line which are subsequently administered to the patient, or used in vitro to produce recombinant cells which are then re-administered to the patient.

The amino acid of the invention may be substantially pure, or contained in a suitable vector or delivery system. The nucleic acid may be DNA, cDNA, PNA, CNA, RNA or a combination thereof. Methods for designing and introducing such a nucleic acid are well known in the art. An overview is provided by e.g. Pascolo S. 2006; Stan R. 2006, or A Mandavi 2006 (see Mandavi A, Monk B J. Recent advances in human papillomavirus vaccines. Curr Oncol Rep. 2006 November; 8 (6): 465-72. Stan R, Wolchok J D, Cohen A D. DNA vaccines against cancer. Hematol Oncol Clin North Am. 2006 June; 20(3): 613-36. Pascolo S. Vaccination with messenger RNA. Methods Mol Med. 2006; 127:23-40). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used.

The present invention thus provides a medicament that is useful in treating disorders of the skin or other epithelia, such as epidermolysis bullosa, cystic fibrosis, pachyonychia congenital, autoimmune diseases, such as psoriasis or neurodermitis, and cancers of the skin.

Another aspect of the present invention then relates to the use of an RTM-molecule according to the present invention, the recombinant expression vector according to the present invention, the recombinant skin cell according to the present invention, or the pharmaceutical preparation according to the present invention for the treatment of a disease selected from disorders of the skin or other epithelia, such as epidermolysis bullosa, cystic fibrosis, pachyonychia congenita, autoimmune diseases, such as psoriasis or neurodermitis, and cancers of the skin. Preferred is the use according to the present invention, wherein said medicament is applied to the skin. A respective method of treatment of a disease as above is also encompassed by the scope of the present invention.

The present formulation is one that is suitable for administration of the respective active compound, in particular an RTM of the present invention by any acceptable route such as topical, oral (enteral), nasal, ophthalmic, subcutaneous, intradermal, intramuscular, intravenous or transdermal. Preferably the administration is s.c., and most preferably topical. Administration may be by infusion pump.

Another aspect of the present invention then relates to a method for correcting a genetic defect in a subject comprising administering to said subject an RTM-molecule according to the present invention, the recombinant expression vector according to the present invention, the recombinant skin cell according to the present invention, or the pharmaceutical preparation according to the present invention. As stated above, the genetic aberration of gene expression of the genes to be targeted are the basis for a variety of disorders and diseases, which can be corrected using the compositions of the present invention.

Additionally, the compositions and methods may also be used to provide a gene encoding a functional biologically active molecule to cells of an individual with an inherited genetic disorder where expression of the missing or mutant gene product produces a normal phenotype. Another inventive application of these compositions and methods is to reprogram genes that play specific roles in a variety of diseases, like autoimmune diseases, as explained above.

The following figures and examples merely serve to illustrate the invention and the present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. The above-mentioned features and those that will be described in the following may be realized according to the present invention either individually or in any combination with each other. All references cited in the text are hereby incorporated in their entirety by reference.

FIG. 1 shows a schematic overview of a RTM molecule that is designed to interact with a selected target pre-mRNA. The RTM comprises a target binding domain, a splicing domain, and a coding domain, which contains the new or modified genetic information to reprogram the pre-mRNA.

FIG. 2 shows a schematic overview of the three possible types of RTMs in an RNA with 24 exons, 1) 5' trans-splicing RTMs which include a 5' splice site. After trans-splicing, the 5' RTM will have changed the 5' region of the target mRNA; 2) 3' RTMs which include a 3' splice site that is used to trans-splice and replace the 3' region of the target mRNA; and 3) double trans-splicing RTMs, which carry one or 2 binding domains along with a 3' and a 5' splice site. After trans-splicing, this RTM would replace one or more internal exons in the processed target mRNA.

FIG. 3 shows the schematic representation of 3' trans-splicing. SMaRT creates a chimeric mRNA through a trans-splicing reaction mediated by the spliceosome between the 5' splice site of an endogenous target pre-mRNA and the 3' splice site of the exogenously delivered pre-trans-splicing RNA molecule. The RTM molecule binds through specific base pairing to an intron of the endogenous target pre-mRNA and replaces the whole 3' sequence of the endogenous gene upstream of the targeted intron with the wild type coding sequence of the RTM.

FIG. 4 shows an RTM molecule for the LacZ double trans-splicing model system as used in the Examples, below. Binding domain sequence: CCGTCCCCACCCACCTGCA-CAGCTCTTCCCTTCCTCTCCTCCAG (SEQ ID No. 3); Spacer sequence: GAGAACATTATTATAGCGTTGCTC-GAG (SEQ ID No. 4); Branch point sequence: TACTAAC; Polypyrimidine tract: TCTTCTTTTTTTTCTG (SEQ ID No. 5); 3' acceptor splice site: CAG.

FIG. 5 shows the construct PTM-6 for endogenous trans-splicing of the COL7A1 gene as described I the Examples, below. Binding domain sequence: (sequence marked in bold: complementary to COL7A1 exon 65) CTTCCTCCCGTCT-TCTCCAGGGTCCCCAGGTTCTCCCT-GTGGGCAGAGGACTCACA TCAGCCCAAACAT-TCACTGGTGTCTGGCTGCAAGACACTACCTTGCTA-GATTTCA GATGACTGTGACTGTATTTCTGTGCCTG-TAGCTATGGTTGTGTGTGTCTTGGAGCA TGGCCT-GTGGCCGTCTGAGTGAGCTGCTACAT-GTCTAGGGGTGTGCCTGCATAGG (SEQ ID No. 16), Spacer sequence: AACGAGAACATTATTATAGCGT-TGCTCGAG (SEQ ID No. 17); Branch point sequence: TACTAAC; Polypyrimidine tract: TCTTCTTTTTTTTCTG (SEQ ID No. 18); 3' acceptor splice site: CAG FIG. 6 shows a light microscopic picture of β-galactosidase stained transfected HEK 293FT cells. Magnification: 100×; A) Transfection of HEK 293FT with Target vector alone did not result in any β-gal activity. B) Accurate trans-splicing between Target pre-mRNA and RTM RNA produced functional β-gal in co-transfected epithelial 293FT cells. 10% of co-transfected cells showed restoration of β-gal expression.

FIG. 7 shows a microscopy analysis of cotransfected HEK 293FT cells. Magnification: 200×. A) Specific trans-splicing between GFP-Target and GFP-PTM-1 in co-transfected cells leads to a complete GFP exon and therefore the cells produce green fluorescence. B) The red fluorescence reporter on the RTM serves as a transfection control and indicates non-specific trans-splicing, cis-splicing or direct expression of unspliced RTM.

FIG. 8 shows the immunofluorescent staining of organotypic skin equivalents with an anti-type VII collagen antibody. Analysis was done in an epifluorescence Zeiss Axioscop microscope. Magnification: 100×, Exposure Time: 10 s. A) Immunofluorescence staining of the SE made with non-treated immortalized RDEB RO keratinocytes and RDEB fibroblasts shows, that the organotypic culture was almost not immunoreactive compared to positive control. B) In SE made with wild type keratinocytes and fibroblasts, the dermal-epidermal junction (DEJ) is strongly reactive, which indicates deposition of collagen type VII. C) Staining to collagen type VII in SE made with clonogenic cells #1 of the reverted RO primary keratinocytes resulted in a highly green signal, which reports deposition of collagen type VII at the DEJ. The intensity of the staining is comparable to that observed in SE made with wild type keratinocytes.

SEQ ID Nos 1 to 26 show the sequences of regions, primers and probes as used in the Examples.

SEQ ID No 27 shows the sequence of the binding domain of the construct PTM13 specific for exon 9 of PLEC1 (Example 3).

SEQ ID No 28 shows the sequence of the binding domain of the construct PTMN9 specific for exon 52 of COL17A1 (Example 3).

SEQ ID No 29 shows the sequence of the construct RTM-BD6 according to the invention for the binding in MMP-9 (Intron 1).

EXAMPLES

Introduction

The 3' trans-splicing method was used as an example in order to demonstrate the successful transfer of RTMs into cells and accurate replacement of an internal exon by a double-trans-splicing between a target pre-mRNA and a RTM for correction of the COL7A1 gene in vitro, because the 3' exon replacement is the most frequently adopted type in the current trans-splicing studies (Chao H. et al. (2003) Phenotype correction of hemophilia A mice by spliceosome-mediated RNA trans-splicing. *Nat. Med.* 9, 1015-1019) (Dallinger G. et al. (2003) Development of spliceosome-mediated RNA trans-splicing (SMaRT) for the correction of inherited skin diseases. *Experimental Dermatology* 12, 37-46) (Liu X. M. et al. (2002) Partial correction of endogenous Delta F508 CFTR in human cystic fibrosis airway epithelia by spliceosome-mediated RNA trans-splicing. *Nature Biotechnology* 20, 47-52) (Mansfield S. G. et al. (2000) Repair of CFTR mRNA by spliceosome-mediated RNA transsplicing. *Gene Ther.* 7, 1885-1895) (Puttaraju M. et al. (1999) Spliceosome-mediated RNA trans-splicing as a tool for gene therapy. *Nat. Biotechnol.* 17, 246-252) (Sullenger B. A. and Gilboa E. (2002) Emerging clinical applications of RNA. *Nature* 418, 252-258). In this process the entire 3' region of the target pre-mRNA is replaced by the coding sequences carried by a 3' RTM.

The RTM base pairs with an intron of the target pre-mRNA through the binding domain, then induces trans-splicing between the adjacent 5' donor splice site of this intron and the 3' acceptor splice site of the RTM by SMaRT. This RTM carries a polyadenylation site (pA) but no ATG initiation codon, which must be acquired from the target pre-mRNA (Mitchell L. G. and McGarrity G. J. (2005) Gene therapy progress and prospects: reprograming gene expression by trans-splicing. *Gene Ther.* 12, 1477-1485).

Figure 1:
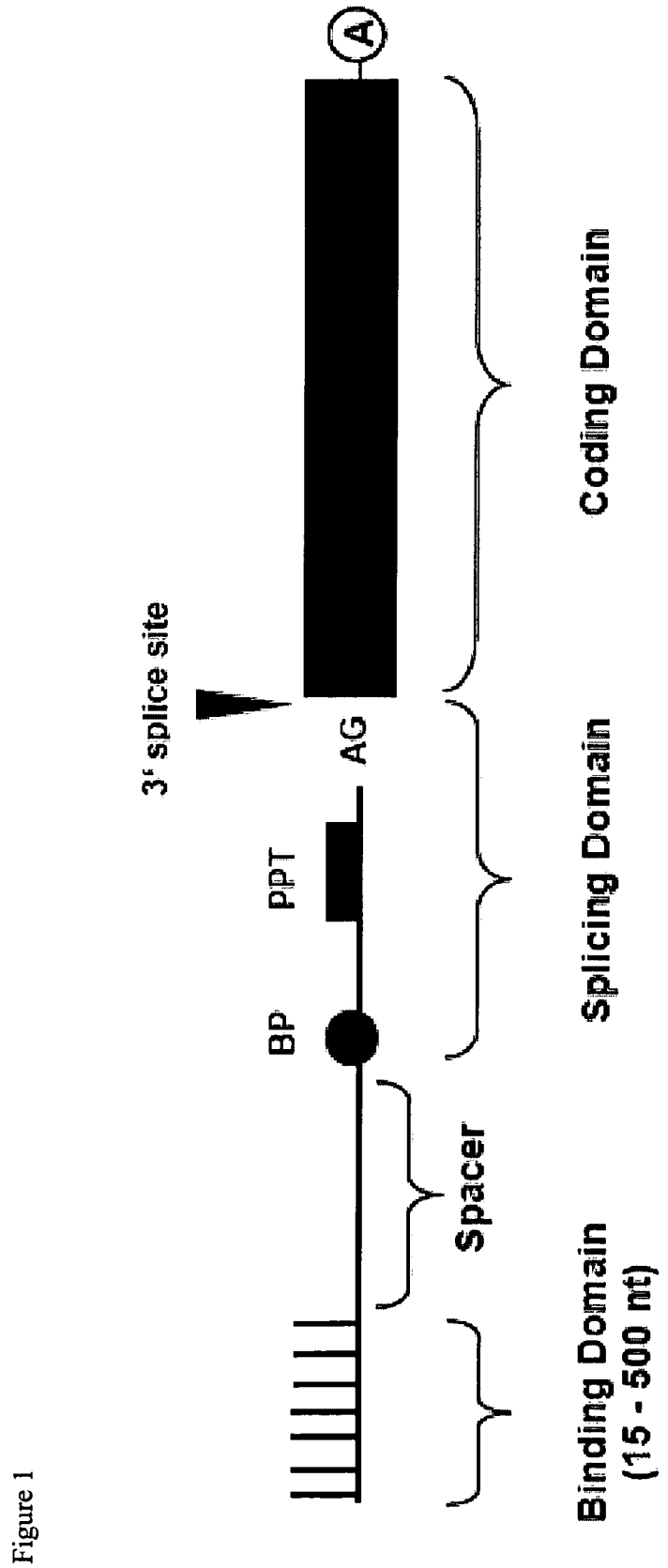
Figure 2:
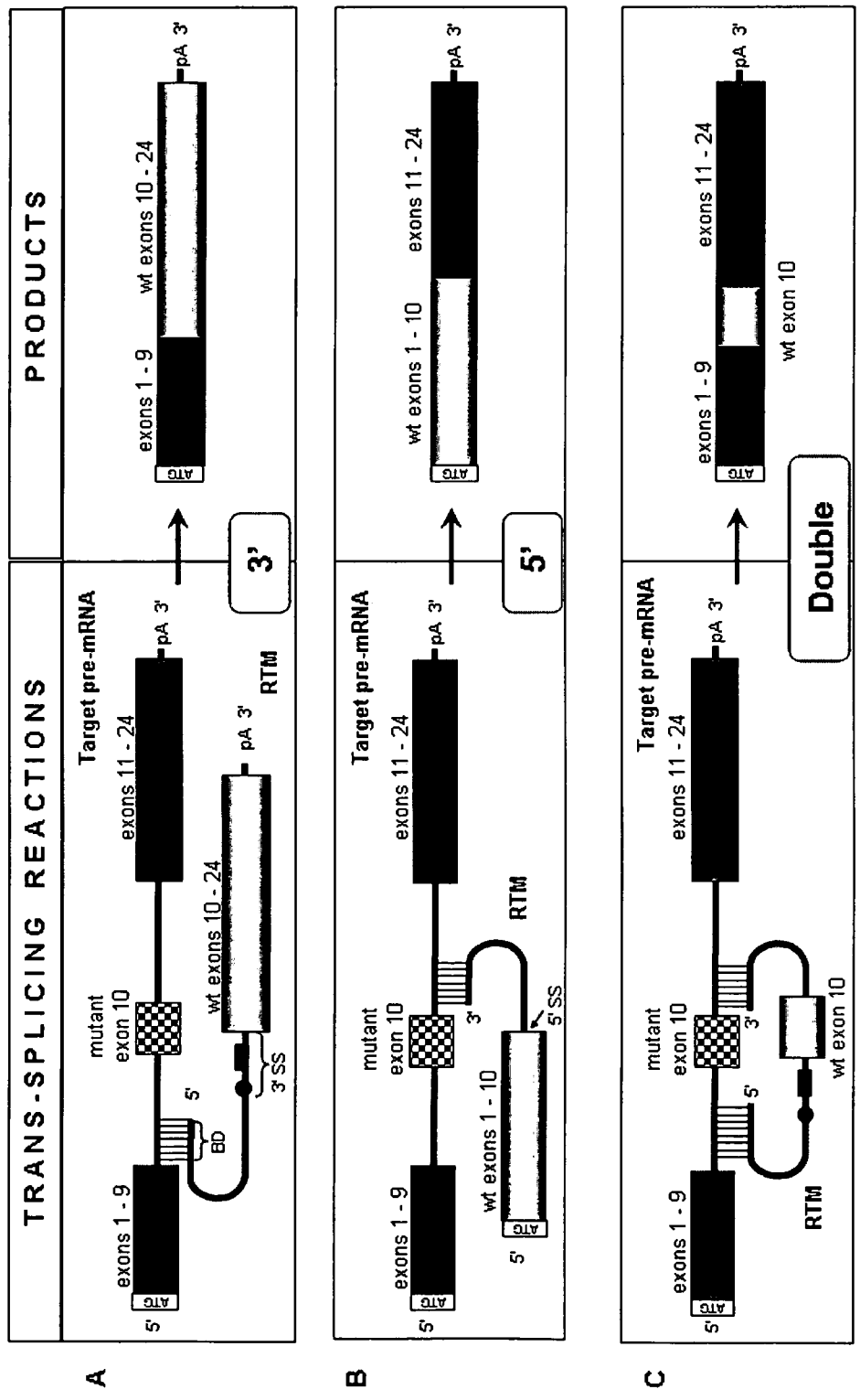
Figure 3:
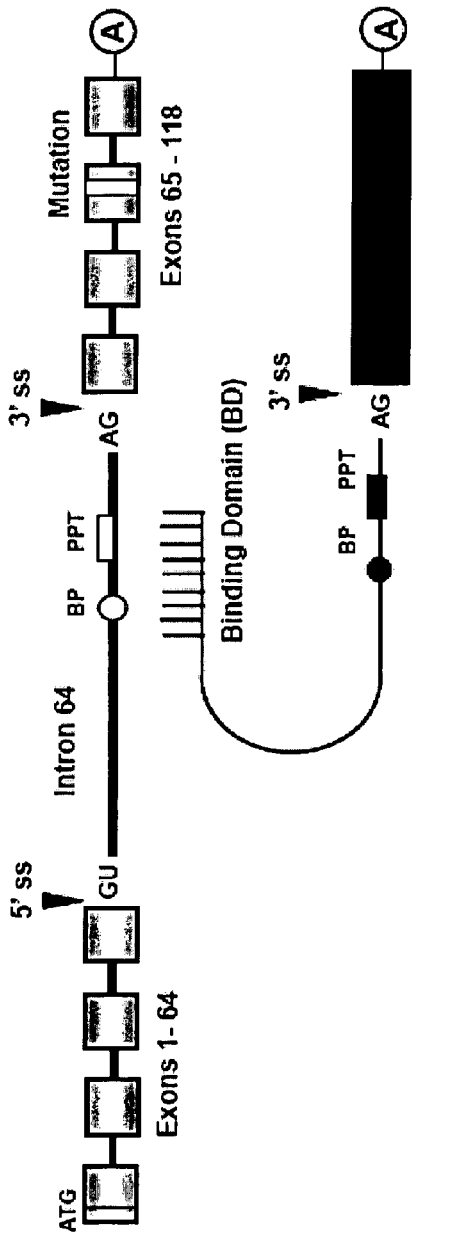

FIG. 3 shows the schematic representation of 3' trans-splicing. SMaRT creates a chimeric mRNA through a trans-splicing reaction mediated by the spliceosome between the 5' splice site of an endogenous target pre-mRNA and the 3' splice site of the exogenously delivered pre-trans-splicing RNA molecule. The RTM molecule binds through specific base pairing to an intron of the endogenous target pre-mRNA, and replaces the whole 3' sequence of the endogenous gene upstream of the targeted intron with the wild type coding sequence of the RTM. This process results in a reprogrammed transcript, consisting of the 3' wild type sequence without the mutation.

Preferred materials and method for performing the experiments whose results are discussed below can be taken from the respective literature, such as, for example, the experimental section of WO 2003/069311, incorporated herewith by reference.

Molecular Cloning Technologies

Reagents for Molecular Cloning

DNA amplifications for cloning were done with Pfu Turbo polymerase (Stratagene, La Jolla, Calif.) in Applied Biosystems 2720 Thermal Cycler. To amplify long PCR fragments (1.6-4 kb) the inventors used the Expand Long Range dNTPack according to the manufacturer's protocol (Roche, Mannheim, Germany). PCR products and digested plasmids were eluted from an 1% agarose gel, and purified using GFX kit (GE Healthcare, Buckinghamshire, UK). DNA was either eluted in $H_2O$ or Tris-EDTA, pH 8.0. All restriction enzymes used for cloning procedures were purchased from New England Biolabs, Beverly, Mass. Ligations were performed either with Promega's T4 DNA Ligase (Madison, Wis.) or T4 DNA Ligase from New England Biolabs (Beverly, Mass.). For dephosphorylation of digested vector ends, Calf Intestine Alkaline Phosphatase (Fermentas, St. Leonrot, Germany) was used. All target and RTM plasmids used for the double trans-splicing model systems were cloned into pcDNA3.1D/V5-His-TOPO vector (Invitrogen, Calrlsbad, Calif.). The plasmids were amplified in chemically competent bacterial strains TOP10 or DH5α (Invitrogen, Calrlsbad, Calif.). Chemically competent XL 10-Gold bacteria (Stratagene, Amsterdam, The Netherlands) were used for amplification of big vectors (up to 14 kb). Plasmid preparations were made using the GenElute™ Plasmid Miniprep Kit from Sigma-Aldrich (St Louis, Mo.) and QIAquick kit (Qiagen, Courtaboeuf, France). The fluorescent reporter genes GFP and DsRed amplified from the vectors pAcGFP1 and pDs-Red Monomer, and the vector pIRES2-AcGFP1 was used as template for amplification of the wild type IRES sequence (Clontech, Saint-Germainen-Laye, France). The restriction enzyme CviJI*, used for construction of a random binding domain library, was purchased from Roboklon (Berlin, Germany). The DNA Terminator End Repair Kit was purchased from Lucigen (Middleton, Wis.). Rneasy Mini kit for RNA isolation of cultured adhesive cells was purchased from Qiagen (Hilden, Germany).

RT-PCR reactions were performed with SuperScript One-Step RT-PCR and SuperScript One-Step RT-PCR for Long Templates with Platinum Taq (Invitrogen). All vector constructs and PCR products were sequenced with an ABI Prism automated sequencer using an ABI PRISM dye terminator cycle sequencing kit (Applied Biosystems, Foster City, Calif.), and 3.2 pmol of primer per reaction to verify sequences. The retroviral vector pLZRS-IRES-Zeo (Nolan and Shatzman 1998 Curr Opin Biotechnol. 1998 October; 9 (5): 447-50) was kindly provided by G. Meneguzzi, Nice, France. Trans-splicing of COL7A1 in a double-transfection model system.

Trans-Splicing in Double Transfection Model Systems

Figure 4:
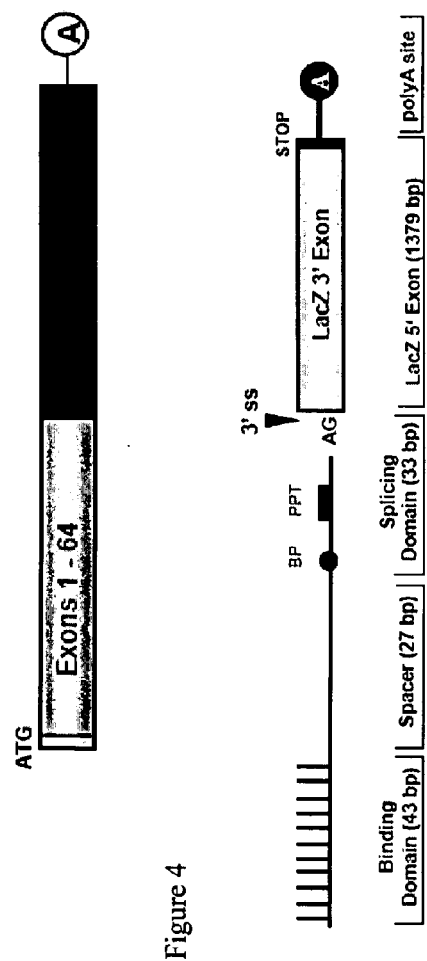
Figure 5:
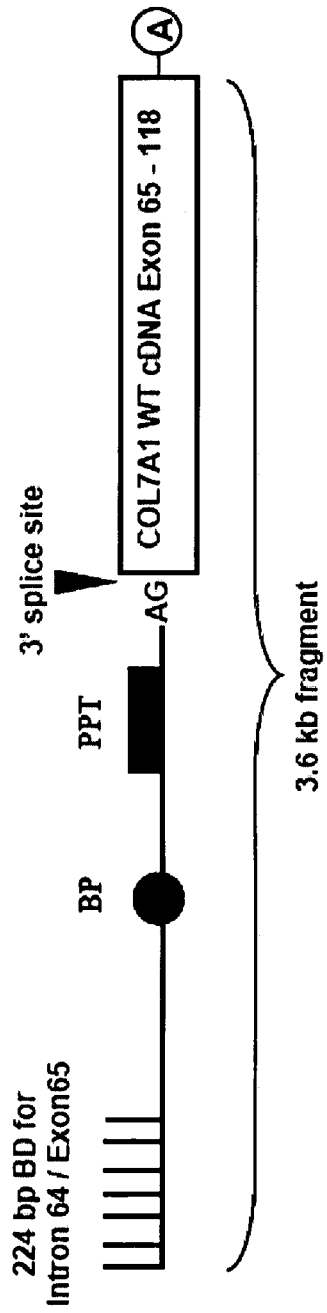

Construction of Vectors for the LacZ Trans-Splicing Model System
Target for LacZ Model System For cloning of the LacZ-Target vector, LacZ-T1 from G. Dallinger (Dallinger G. et al. (2003) Development of spliceosome-mediated RNA trans-splicing (SMaRT) for the correction of inherited skin diseases. *Experimental Dermatology* 12, 37-46) was digested with BamHI and BstEII (New England Biolabs). The LacZ-Target includes a LacZ 5' exon (1-1788 bp) followed by intron 43 of the Collagen 7 gene (359 bp) and a LacZ 3' exon (1789-3174 bp). The 3' LacZ exon contains two in frame stop codons at position 1800 bp. Intron 43 of COL7A1 was amplified by PCR with Pfu Turbo DNA polymerase (Stratagene) using human genomic DNA as template and primers Int43F (5'-GGATCCGTAAACCCACTG-GCTGCAATG-3'; SEQ ID No. 1) and Int43R (5'-GGTTAC-CTGGAGGAGAGGAAGGGAAGA-3'; SEQ ID No. 2). Genomic DNA was isolated with Puregene™ DNA Purification Kit (Gentra Systems, Minneapolis, Minn.). The fragment was digested with BamHI and BstEII (New England Biolabs) and inserted between the two LacZ exons using T4 DNA Ligase (Promega) for 3 h at room temperature in 204
RTM for LacZ Model System The LacZ-PTM was constructed by digesting pCOL17-PTM, pcDNA3.1D/V5-His-TOPO vector (Dallinger G. et al. (2003) Development of spliceosome-mediated RNA trans-splicing (SMaRT) for the correction of inherited skin diseases. *Experimental Dermatology* 12, 37-46.), with EcoRI and KpnI (New England Biolabs) and replacing the COL17A1 binding domain with an oligonucleotide containing a 43 bp antisense binding domain (BD) for COL7A1 intron 43. Beside the BD, the LacZ-PTM contains a 27 bp spacer sequence, a branch point (BP), a polypyrimidine tract (PPT), followed by the 3' splice acceptor site CAG and the 3' LacZ exon without STOP codons (see FIG. 4).
Construction of Vectors for the Fluorescence Trans-Splicing Model System
Target for Fluorescence Model System The target for the fluorescence screening procedure consists of the 5' half of a GFP exon and intron 64 and exon 65 of COL7A1. The 5' part of GFP (1-336 bp) was amplified from the vector pAcGFP1 (Clontech) using Pfu Turbo DNA Polymerase (Stratagene). The reverse primer was designed to insert a 5' splice site (gtaag) at the GFP/intron border to be used for trans-splicing the target intron, as well as an EcoRV restriction site. (5'GFP F: 5'-CACCATGGTGAGCAAGGG-3' SEQ ID No. 6; 5'GFP R: 5-GATATCTCTTACCTCG-GCGCGACTT-3' SEQ ID No. 7) The 5' GFP fragment was cloned into the TOPO cloning site of pcDNA3.1D/V5-His-TOPO vector (Invitrogen) according to manufacturer's instructions.

Intron 64 and exon 65 were amplified from human genomic DNA with the following primer pair: Int64F including an EcoRV site: 5'-GATATCGTGAGTGTGTCCAGGGCA-3' SEQ ID No. 8, and Int64R including a NotI site: 5'-GCGGC-CGCCTTCCTCCCGTCTTCTCC-3' SEQ ID No. 9. Vector and PCR fragments were both cut with EcoRV and NotI and ligated using NEB T4 DNA Ligase for 1 h at RT
RTM for Fluorescence Model System For construction of the RTM vector, 3' GFP (337-720 bp) was amplified from the pAcGFP1 vector (Clontech) using primers designed to insert a PPT sequence and a KpnI restriction site at the 5' end and a HindIII restriction site at the 3' end of the fragment (#384F: 5'-GGTACCTCTTCTTTTTTTTCT-GCAGGTGAAGTTCGAGGGCGAT-3' SEQ ID No. 10 and #385R 5'-AAGCTTACACCAGACAAGTTGGTAATG-3' SEQ ID No. 11). PTM-5 from G. Dallinger (Dallinger G. et al. (2003) Development of spliceosome-mediated RNA trans-splicing (SMaRT) for the correction of inherited skin diseases. *Experimental Dermatology* 12, 37-46) containing a 27 bp spacer and a BP sequence just upstream of the KpnI restriction site, was digested with KpnI and HindIII for ligation of the amplified product. The second cloning step was the ligation of the 3' GFP, including spacer, BP and PPT sequences into the TOPO site of pcDNA3.1D/V5-His-TOPO vector (Invitrogen). The 470 bp fragment was amplified using a forward primer, carrying an EcoRI and a HpaI restriction site (5'-CACCGAATTCATCGATGTTAACGAGAA-CATTATTATAGCGTTG-3' SEQ ID No. 12). The HpaI sequence was inserted to serve as restriction site for blunt ligations of variable binding domains. The reverse primer was 5'-GCTCACTTGTACAGCT-3' SEQ ID No. 13. The resulting vector was used as target vector for the following cloning steps. The wild type IRES sequence was amplified from vector pIRES2-AcGFP1 and ligated between EcoRV and XmaI restriction sites. Following primers were used: IRES F: 5'-ggatccgatatcatccgcccctctcc-3' SEQ ID No. 14; IRES R: 5'-CCCGGGAGGTTGTGGCCATATTATCATC-3' SEQ ID No. 15. The full length DsRed gene was cut out from the vector pDs-Red Monomer (Clontech) using EcoRV and NotI restriction enzymes and cloned into the RTM vector between those two restriction sites.
Trans-Splicing in the Endogenous COL7A1 Gene
Construction of Vectors for Endogenous Trans-Splicing
Cloning of the COL7A1 Exon Sequence into the RTM Vector The pre-trans-splicing molecule (RTM) for endogenous trans-splicing consists of a 224 bp binding domain (BD), complementary to intron 64 and exon 65 of COL7A1, a 31 bp spacer, a branch point (BP) and a polypyrimidine tract (PPT) followed by a 3' splice acceptor site (CAG) and the 3' wild type coding sequence (5648-8951 bp) of human COL7A1. The 300 bp sequence spanning the BD, spacer, BP and PPT was amplified from the FACS selected RTM and cloned into pcDNA3.1D/V5-His-TOPO (Invitrogen) into the TOPO cloning site. The forward primer was designed to introduce an EcoRI restriction site while the reverse primer introduced a single NheI site for further cloning strategies. The 3.3 kb 3' sequence of human COL7A1, consisting of exon 65 to exon 118 of an unaffected person, was amplified by a one-step reverse transcriptase PCR (SuperScript One-Step RT-PCR for Long Templates with Platinum Taq; Invitrogen). The amplified product was digested with NheI and EcoRV and cloned into the RTM vector. The whole construct was analyzed by sequencing to confirm its correct sequence.

Subcloning of the RTM into Retroviral Vector pLZRS-IRES-Zeo

For stable transduction, the RTM was subcloned into the MuLV-derived pLZRS-IRES-Zeo retroviral vector (kindly provided by G. Meneguzzi, Nice) (Michiels F. et al. (2000) Expression of Rho GTPases using retroviral vectors. *Regulators and Effectors of Small Gtpases, Pt D* 325, 295-302) between the EcoRI and SNaBI restriction sites. Retroviral constructs were generated by digesting vector and insert with the appropriate restriction enzymes, gel purification and ligation with T4 DNA Ligase (New England Biolabs) for three hours at room temperature. Plasmids were amplified in the *E. coli* XL10-Gold strain (Stratagene), purified with a QIAquick kit (Qiagen) and subjected to sequencing.

Transfection of Target and RTM into HEK 293FT Cells

HEK 293FT cells were used for double-trans-splicing experiments because of their lack of endogenous COL7A1 mRNA. Double-transfections of LacZ Target and RTM plasmids (2 µg each) were performed using LipofectaminePlus reagent (Invitrogen) according to manufacturer's protocol. The day before transfection, $3 \times 10^5$ cells were plated on 60 mm plates and grown in antibiotic-free DMEM for 24 h. Cells were analyzed 48 h after transfection. 1 µg of the fluorescent Target and 3 µg of a prepared fluorescent RTM library, or rather a fluorescent RTM vector, consisting of a single binding domain, was transiently transfected into 293FT cells using EcoTransfect™ (OZ Biosciences). $10^6$ cells were used for transfections according to the manufacturer's protocol. Analysis in fluorescent microscope and FACS were done 48 h post transfection.

Analysis of Trans-Splicing in the LacZ Model System

Protein Preparation and β-gal Assay

Total protein from the transfected cells was isolated by a freeze and thaw method. For determination of β-gal activity the inventors used the Invitrogen β-gal assay kit (Invitrogen). Total protein concentration was measured by the dye-binding assay according to Bradford using Bio-Rad protein assay reagent (Bio-Rad).

In Situ Staining for β-gal

The expression of functional β-gal was monitored using a β-gal staining kit (Invitrogen) following the manufacturer's protocol. The percentage of β-gal positive cells was determined by counting stained versus unstained cells in five randomly selected fields. (Dallinger G. et al. (2003) Development of spliceosome-mediated RNA trans-splicing (SMaRT) for the correction of inherited skin diseases. *Experimental Dermatology* 12, 37-46).

Analysis of Trans-Splicing in the Fluorescent Model System

Visualization of Trans-Splicing in Fluorescent Microscope and FACS

Trans-splicing in cells was verified in an epifluorescence Zeiss Axioskop microscope (Carl Zeiss). For trans-splicing analysis in FACS $10^6$ cells were washed with cold FACS buffer (Dulbecco's PBS, 3% FCS) and resuspended in 1 ml FACS buffer and kept on ice. Before analysis the cells were stained with 10 µl 7-AAD (Beckman Coulter) for 5 min on ice and 25,000 events were analyzed using the Beckman Coulter FC500. CXP software was used for data analysis.

Analysis of Accurate Trans-Splicing on mRNA Level

Accurate trans-splicing between the fluorescent Target and RTM vectors was analyzed by sequencing. Total RNA of HEK 293FT cells transiently co-transfected with Target and RTM was isolated 48 h after transfection using Rneasy Mini Kit (Qiagen). Cis-splicing of the target was analyzed by RT-PCR (SuperScript One-Step RT-PCR, Invitrogen), using a forward primer (#666 F: 5'-GCCACTACGGCAAGC-3'; SEQ ID No. 19) complementary to a sequence of the 5' GFP, and a reverse primer (#667 R: 5'-CCGTCTTCTC-CAGGGTC-3'; SEQ ID No. 20) complementary to a sequence of COL7A1 exon 65 on the Target.

Cell Culture and Analysis in the Endogenous Trans-Splicing Model

Retroviral Infection of Human Keratinocytes with the pLZRS-RTM Vector

Amphotropic Phoenix packaging cells (Phoenix-ampho) were used to generate infectious retroviral particles (Michiels et al. 2000). The recombinant plasmid pLZRS-PTM was introduced into Phoenix-ampho cells by transient calcium phosphate transfection. The pLZRS-PTM recombinant viruses were harvested from cell culture medium 48 h after transient transfection (titer approximately $2.5 \times 10^6$ CFU/ml) (Gache et al. 2004). Cultures of RDEB ROB keratinocytes ($2 \times 10^5$ cells/cm$^2$) were infected with the viral suspension in the presence of 5 µg/ml of polybrene at 32° C. in humid atmosphere, 5% CO$_2$. Fresh culture medium was added 2 h later and cells were incubated overnight at 32° C. Keratinocytes were selected in the presence of 200 µg/ml Zeocin (Invitrogen) for 7 days. The selected cells were passaged and processed for further studies.

Isolation of Clonogenic Cells

Subconfluent cultures of transduced RO RDEB keratinocytes at passage 2 after Zeocin selection were used for the isolation of single clonal cell types. For this purpose dilutions of $10^3$, $2 \times 10^3$, and $5 \times 10^3$ transduced RO keratinocytes were seeded in 75 cm2 petri dishes onto regular feeder layers for growth in culture over 14 days. Cell colonies with regular perimeters and large diameters (about 1 cm$^2$) were isolated, trypsinized, and expanded for further analysis.

Analysis of RTM Integration into the Keratinocytes Genome

Preparation of Genomic DNA from Cells $5 \times 10^6$ cells were washed with phosphate buffered saline (PBS), trypsinized using 1% Trypsin-EDTA (Biochrom) and pelleted by centrifugation. Genomic DNA was isolated with Dneasy Blood and Tissue Kit (Qiagen) according to the manufacturer's protocol and diluted in 200 µl elution buffer.

PCR Analysis of Genomic DNA

The inventors used 1 µl of the isolated genomic DNA for PCR reaction using Expand Long Range dNTPack (Roche). A 3.6 kb fragment was amplified with vector specific primers. The forward primer (#2221 F 5'-AGACGGCATCGCAGCT-TGG-3'; SEQ ID No. 21) binds to the pLZRS-PTM vector backbone sequence upstream the RTM binding domain, and the reverse primer (#816 F 5'-TCTAGAGAATTCTCAGTC-CTGGGCAGTACCTG-3'; SEQ ID No. 22) is complementary to the last exon of COL7A1 on the pLZRS-PTM vector. A second PCR was performed to verify the chromosomal integration of the pLZRS-PTM and to exclude the possibility of amplification of an episomal replicated pLZRS-PTM vector. For this test the inventors used primers which bind outside the LTR region of the retroviral RTM vector (EBNA-1 F: 5'-ATGTCTGAGAGGGGCCAG-3'; SEQ ID No. 23; EBNA-1 R: 5'-CTCCTGCTCCTGTTCCACC-3'; SEQ ID No. 24). A 280 bp fragment would be amplified, if the viral genome was present in episomal configuration. For positive controls the inventors used 1 µl of a pLZRS-PTM plasmid preparation respectively. Fragments were analyzed on an 1% agarose gel.

Analysis of RTM Expression on the RNA Level

Preparation of Total RNA from Cells

Cells ($4\times10^6$) at passage 2 after infection were rinsed with PBS once, trypsinized, pelleted and total RNA was isolated using RNAqueous kit (Ambion). Contaminated plasmid and genomic DNA were eliminated by treating with Dnase I (Sigma-Aldrich).

Sequencing Analysis

From sequencing analysis of pLZRS-PTM the inventors learned, that the vector harbours two polymorphisms on the COL7A1 sequence, which were not detected on the endogenous COL7A1 transcript of RO RDEB kerationocytes. To verify if the RTM was expressed in the transduced cells, the inventors performed sequencing analysis of the desired COL7A1 region using total RNA of RTM transduced and non-transduced cells. Primers were designed to amplify a 532 bp RT-PCR product including the polymorphisms at position 8274 and 8615 on the COL7A1 transcript (P2 F: 5'-CAAGGGTGACCAGGGCGA-3'; SEQ ID No. 25, and P2R: 5'-CCAAGGAGCTTCAGGGTCC-3'; SEQ ID No. 26).

EXAMPLE 1

Trans-Splicing in a LacZ Model System

The feasibility of 3' trans-splicing in correcting the COL7A1 gene has been established using a LacZ trans-splicing model repair system. In this system the inventors used intron 43 of COL7A1 as the Target for trans-splicing. The intron is flanked by the 5' exon of the LacZ gene and the 3' exon which contains two in-frame stop codons. Because of the stop codons, cis-splicing of the Target leads to a defective RNA transcript and therefore doesn't produce functional β-galactosidase. The second construct of the LacZ model repair-system is the RTM, consisting of a 43 bp antisense binding domain for intron 43 and the 3' LacZ exon without the stop codons. Precise trans-splicing between Target and RTM in double-transfected cells replaces the mutant 3' exon of the Target and therefore restores β-gal activity.

Analysis of Protein Function Restoration

Figure 6:
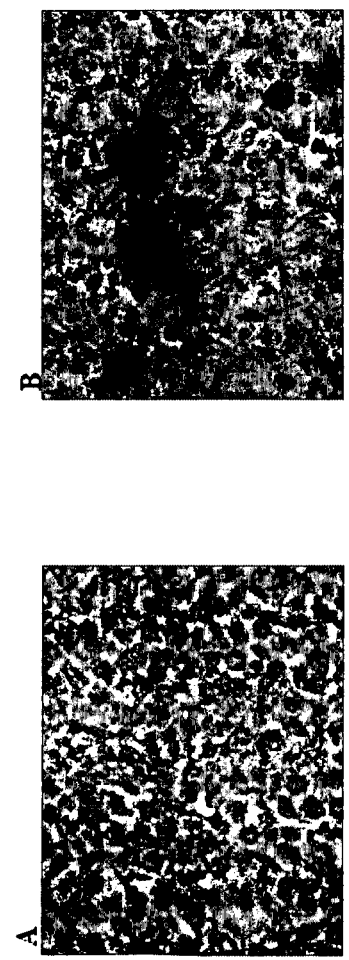

The inventors transiently co-transfected 293FT cells with Target and RTM plasmid for investigation of the repair of defective LacZ pre-mRNA by SMaRT and production of functional β-gal protein. In situ staining of cotransfected 293FT cells revealed 10% β-gal positive cells of total cells, which indicates corrected RNA produced by functional trans-splicing between Target and RTM. In contrast, cells transfected with either LacZ-Target or RTM alone did not produce any functional β-gal as noticed by the complete absence of β-gal positive cells. For further quantification of the produced β-gal amount, the β-gal enzyme activity was measured in a colorometric assay using 293FT cell lysates 48 h after transfection. β-gal activity in protein extracts prepared from cells transfected with either 2 µg of the LacZ-Target or RTM alone almost corresponded to the background level. In contrast, cells co-transfected with both constructs showed a 20 fold increase of β-gal activity compared with controls. See also FIG. 6 for results.

EXAMPLE 2

Trans-Splicing in a Fluorescent Model System

The ability of RTM-induced trans-splicing to repair the COL7A1 pre-mRNA was further examined in a fluorescent-based transient co-transfection assay. In this trans-splicing model, a green fluorescence protein (GFP) is expressed in case of accurate trans-splicing. For this system, the inventors constructed a Target vector comprising the 5' half of a GFP exon, intron 64 of COL7A1, and COL7A1 exon 65. The RTM consists of a binding domain (randomly designed, see below), complementary to a sequence of COL7A1 intron 64, the 3' splicing domain including branch point (BP) and polypyrimidine tract (PPT), followed by the 3' half of GFP. Downstream of the hemi-GFP exon the inventors inserted an internal ribosomal entry site (IRES) and a full-length DsRed gene, which acts as a control reporter in transfected cells. Precise trans-splicing between Target and RTM in co-transfected cells leads to an entire and functional GFP exon, which can be examined directly in a fluorescent microscope or in FACS.

Analysis of Protein Function Restoration

Figure 7:
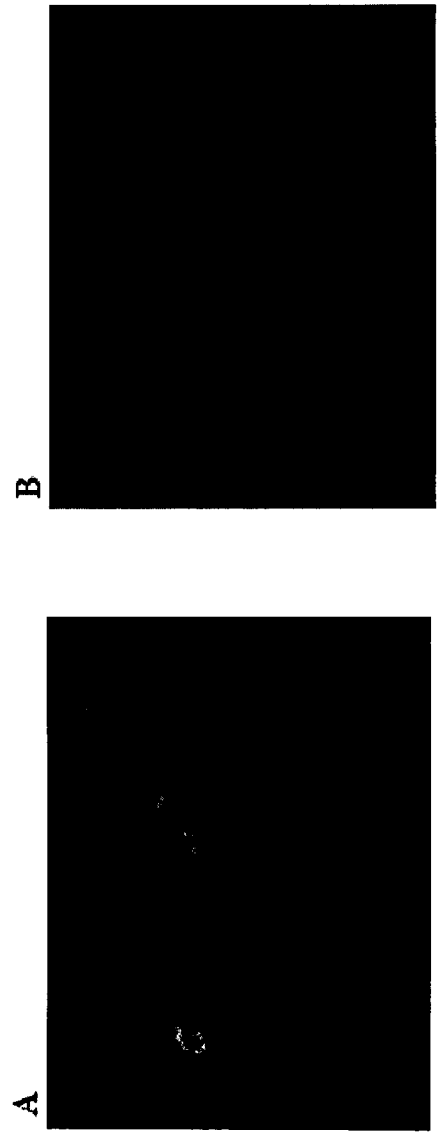

The feasibility of trans-splicing the COL7A1 gene in intron 64 has been proven in a co-transfection assay in HEK 293FT cells. The inventors transiently transfected the target vector comprising the sequence of intron 64 and one part of the green fluorescence protein with a single RTM molecule consisting of a 42 base pair antisense binding domain and the second part of the green fluorescence protein, as well as an entire DsRed gene (GFP-PTM-1). The binding domain was designed manually to bind through base pairing in the 5' region of the intron. Analysis of co-transfected cells under a fluorescence microscope 48 h after transfection revealed a trans-splicing efficiency of about 10% of all transfected cells. See also FIG. 7 for results.

Analysis of Accurate Trans-Splicing on RNA Level

To verify, if trans-splicing between GFP-Target and GFP-PTM-1 leads to a correctly trans-spliced GFP exon, the produced RNA was examined by sequencing analysis. HEK 293FT cells were transfected with GFP-Target alone, as well as cotransfected with GFP-Target and GFP-PTM-1, consisting of a 43 bp BD for COL7A1 intron 64. Total RNA was isolated 48 h post-transfection and RT-PCR analysis was performed using either a cis-specific, or trans-specific primer pair. Sequencing of the trans-spliced RT-PCR product demonstrated, that trans-splicing was accurate between GFP-Target and GFP-RTM.

Endogenous Trans-Splicing in the COL7A1 Gene

The construct PTM-6 was selected for the application in endogenous trans-splicing of the COL7A1 pre-mRNA in DEB patient keratinocytes. To achieve efficient transfections of the cells, the inventors cloned the binding domain and 3' splicing elements of PTM-6, followed by the wild type cDNA sequence of COL7A1 exon 65 to exon 118, into the retroviral vector pLZRS-IRES-Zeo (pLZRS-PTM).

Infection of Human Keratinocytes with the pLZRS-PTM Vector

Trans-splicing in the endogenous COL7A1 gene was evaluated in type VII collagen-deficient keratinocytes derived from two different RDEB patients, named KU and RO. KU keratinocytes are homozygous for a nonsense mutation in COL7A1 exon 105 and therefore present optimal target cells for 3' trans-splicing in intron 64. RO keratinocytes carry two heterozygous nonsense mutations in COL7A1 exons 14 and 104. Primary KU and RO keratinocytes, as well as immortalized RO keratinocytes were infected with virus particles encoding the RTM.

Selection of RTM Transduced RDEB Keratinocytes

After antibiotic selection for stably transfected keratinocytes, the cells were amplified for a series of analysis to reveal successful trans-splicing. Unfortunately, the transduced and selected KU primary keratinocytes died in culture after twice-passaging, so that the inventors could not perform the following trans-splicing analysis in those treated patient cells. To achieve long-term serial propagation of the transduced RO keratinocytes for further trans-splicing analysis, the inventors performed single cell cloning on cell pools to isolate keratinocytes, that display the differentiation and clonogenic potential of epidermal clonogenic cells (Barrandon Y. and Green H. (1987) Three clonal types of keratinocyte with different capacities for multiplication. *Proc Natl Acad Sci USA* 84, 2302-2306). The inventors could isolate and expand 7 clones from the transduced RO primary keratinocytes.

Analysis of RTM Expression in Transduced Keratinocytes

Sequencing analysis of the pLZRS-PTM vector prior to infection gave notice about two polymorphisms (silent) on the COL7A1 coding sequence of the RTM, which were not present on the endogenous COL7A1 sequence of RO keratinocytes. This information was used to detect on the mRNA level whether the RTM was expressed in the transduced cells. The inventors performed RTPCR of mRNA prepared from non-transduced and transduced RO keratinocytes with adjacent sequencing of the desired polymorphic region.

The resulting sequence of RTM transduced RO cells and cell line was homozygous for the polymorphisms. This result does not provide the information if trans-splicing occurred in the transduced keratinocytes, but it confirms that the RTM is endogenously expressed in those cells.

Immunofluorescence Staining of Cultured Cells

To verify if protein expression in the transduced keratinocytes could be restored by trans-splicing, the inventors performed an immunofluorescent staining to type VII collagen in the cultured cell pools. The staining to type VII collagen was positive in numerous of the analyzed transduced keratinocytes. This experiment proved that type VII collagen deficient RO keratinocytes regained their ability to produce a functional type VII collagen protein because of accurate trans-splicing between the endogenous COL7A1 pre-mRNA and the introduced RTM.

Western Blot Analysis of Reverted Keratinocytes

Western blot analyses were done to confirm the restoration of a functional type VII collagen in RTM transduced RO keratinocytes by trans-splicing. Immunoblot analyses were performed using the media of cultured cells to detect the expression of type VII collagen as a secreted protein of 290 kDa. A slight band in the right size could be detected in the spent medium of cultured wild type keratinocytes used as a positive control. This band was completely absent in the parental RDEB RO cell-line and primary cells. A strong specific band was detected in reverted immortalized and primary RO keratinocytes. These outcomes give evidence, that trans-splicing in RTM infected RO keratinocytes resulted in the expression of the 290 kDa type VII collagen protein.

Immunofluorescence Staining of Generated Skin Equivalents

Figure 8:
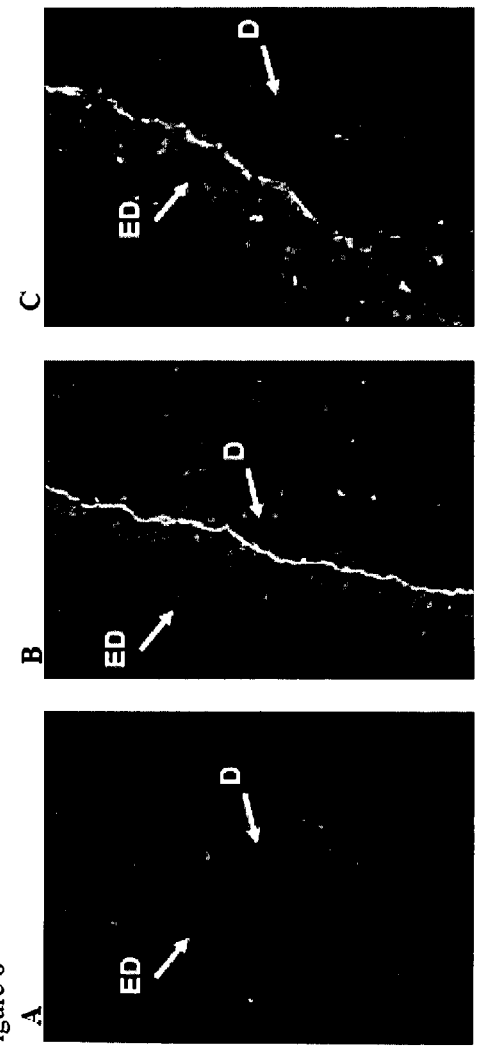

In the next step the inventors constructed skins equivalents (SE) to check if the reverted keratinocytes regained their ability to secrete and deposit type VII collagen at the dermal-epidermal junction. The inventors prepared artificial skins by seeding the reverted keratinocytes on a fibrin matrix containing human type VII collagen deficient RDEB fibroblasts. For a negative control the inventors constructed SE with the parental non-transduced immortalized RO keratinocytes and for a positive control the inventors seeded wild type keratinocytes onto a fibrin gel matrix with embedded wild type fibroblasts. Immunoflourescent staining of the SE using an anti-collagen type VII antibody was performed four weeks after lifting the skin to the air-liquid interface. The staining to type VII collagen in skin equivalents composed of transduced RO primary keratinocytes cell pool (FIG. 8 C) as well as clone 1 of transduced RO cells (data not shown) was positive, which indicates deposition of type VII collagen in the basement membrane.

As can be seen from the above experiments, the present invention enables the use of an RTM of the present invention derived from group of CFTR, integrins, TNF-alpha, interleukins, the immunoglobulin superfamily, kallikreins, matrix metalloproteinases, keratins, collagens, and laminins for the treatment of epidermolysis bullosa and related diseases, such as muscular dystrophy, cancer, and Ehlers Danlos syndrome (see Pfendner, E.; Uitto, J.: Plectin gene mutations can cause epidermolysis bullosa with pyloric atresia. *J. Invest. Derm.* 124: 111-115, 2005, and references as cited therein, Varki, R.; Sadowski, S.; Uitto, J.; Pfendner, E.: Epidermolysis bullosa. Type VII collagen mutations and phenotype-genotype correlations in the dystrophic subtypes. *J. Med. Genet.* 44: 181-192, 2007, and references as cited therein; Jonkman, M. F.; Pas, H. H.; Nijenhuis, M.; Kloosterhuis, G.; van der Steege, G.: Deletion of a cytoplasmic domain of integrin beta-4 causes epidermolysis bullosa simplex. *J. Invest. Derm.* 119: 1275-1281, 2002, and references as cited therein, and Wally V, Klausegger A, Koller U, Lochmüller H, Krause S, Wiche G, Mitchell L G, Hintner H, Bauer J W. 1: J Invest Dermatol. 5' trans-splicing repair of the PLEC1 gene. 2008 March; 128(3): 568-74. Epub 2007 Nov. 8—in particular for 5' splicing; Hengge UR. SMaRT technology enables gene expression repair in skin gene therapy. J Invest Dermatol. 2008 March; 128 (3): 499-500). The data furthermore supports and enables a similar function of the genes as found in the same group (see tables as above) as the genes Keratin 5, Laminin A3, B3, g2, Integrin β4, and α6 in epidermolysis bullosa and related diseases, such as diseases of skin adhesion.

Based on the above disclosure and the references as cited herein, the person of skill will be readily able to design and use RTM-constructs similar to those as exemplary described above in order to provide effective RTM-molecules for the treatment of diseases that are related to mammalian genes of the group of CFTR, integrins, TNF-alpha, interleukins, the immunoglobulin superfamily, kallikreins, matrix metalloproteinases, keratins, collagens, and laminins, as described above.

EXAMPLE 3

Figure 9:
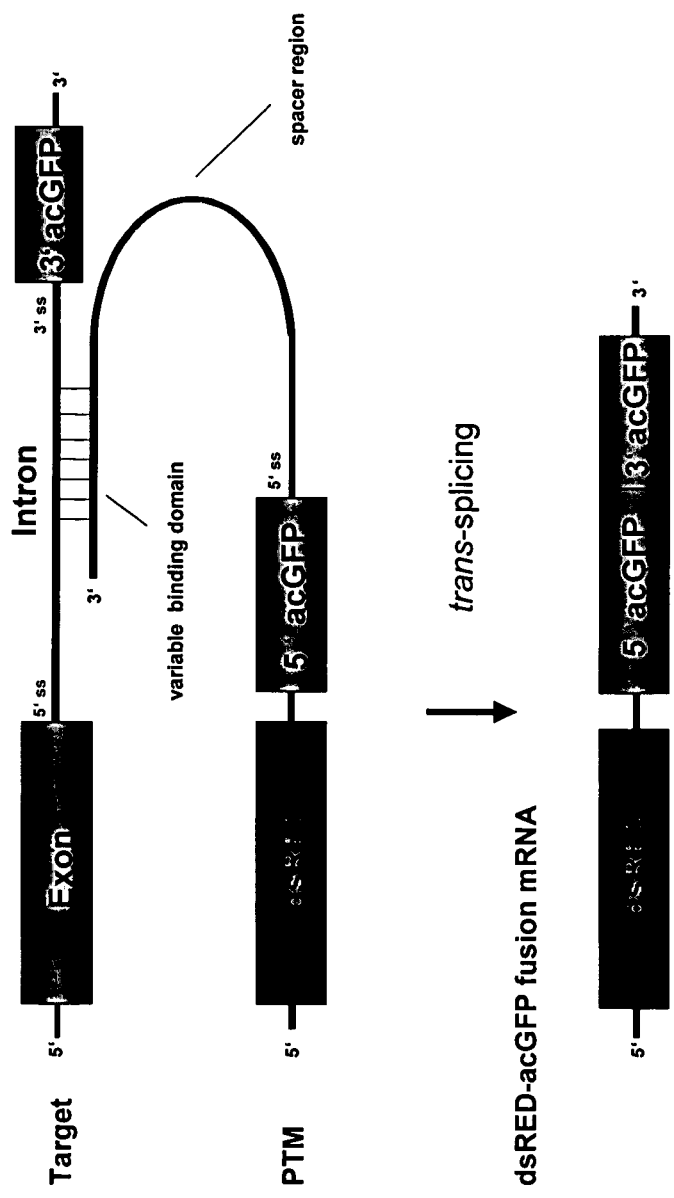
FIG. 9 shows the schematic diagram of 5' RTM and target molecule in the fluorescent model system as used in the examples. The RTM induced trans-splicing events lead to the expression of a dsRED-acGFP fusion protein in RTM and target molecule transfected HEK293 cells.

Efficient Trans-Splicing into Exon 9 of PLEC1 and Exon 52 of COL17A1, Compared to Intronic/Exonic Splicing Efficiency A fluorescent reporter system was used to identify most functional RTMs specific for exon/intron 9 of PLEC1 and exon/intron 52 of COL17A1, wherein a screening system was established that is built up by an intron specific target molecule and a PTM library. The RTM contains a variable binding domain that base pairs with the target intron or upstream exon thereby inducing the recombination of both pre-mRNAs by trans-splicing (see FIG. 9).

The evaluation of trans-splicing efficiency took place using FACS analysis and real time PCR. At least two days after introduction of screening molecules into HEK293 cells, fluorescence microscopy and "Fluorescence Activated Cell Sorting" (FACS) analysis revealed the functionality of the RTMs according to their binding properties to the target intron. The expression of GFP should represent the total amount of specific trans-splicing events, whereas dsRED expression correlated with non-specific trans-splicing events. Besides FACS analysis, the functionality of RTMs with dissimilar binding behavior to the target intron can be investigated on mRNA level by real time PCR. RNA trans-splicing induced recombinations of the target molecule and the RTM led to the fusion of the 5' GFP part of the PTM to the 3'GFP part of the target molecule. Therefore, the amplification of GFP fusion mRNA molecules incorporates the trans-splicing efficiency of single RTMs.

PLEC1

After an evaluation of the trans-splicing efficiency by FACS analysis after double transfection of HEK293 cells with single RTM and target molecule, it was surprisingly found that the efficiency for construct PTM2 (specific for exon/intron 9 of PLEC1) was 89% (i.e. 89% of RTM transfected cells expressed GFP), whereas the efficiency for construct PTM13 (specific for exon 9 of PLEC1) was 99% (i.e. 99% of RTM transfected cells expressed GFP).

Figure 10:
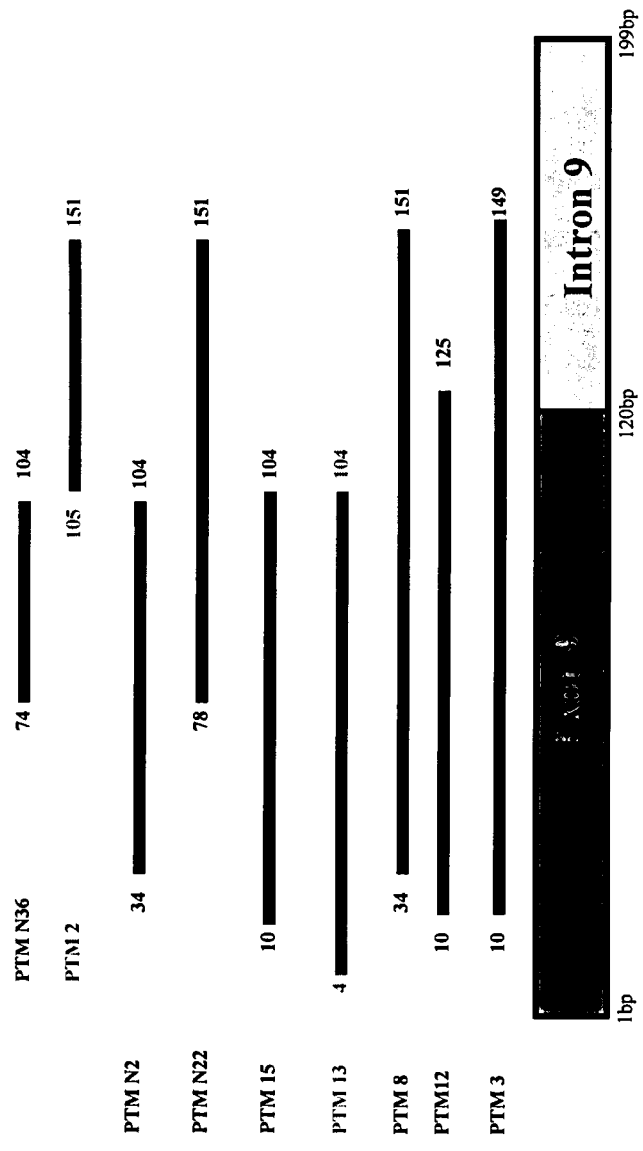
FIG. 10 shows the positions of RTM clones specific for the exon/intron region 9 of the gene PLEC1.
Figure 11:
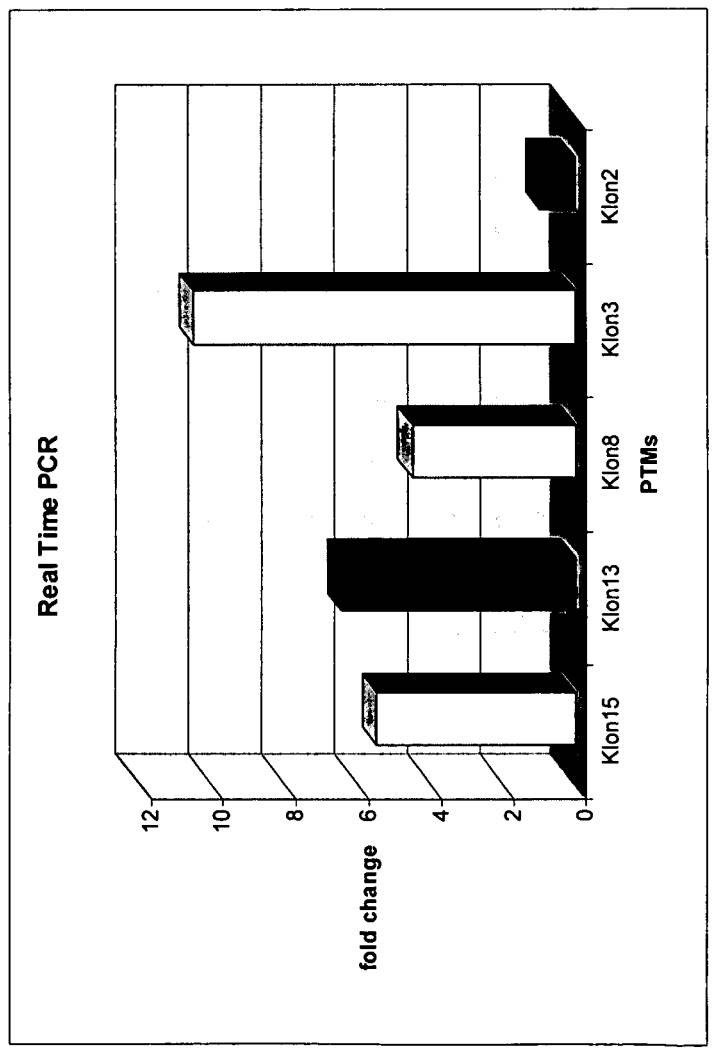
FIG. 11 shows the results of GFP expression for RTM clones specific for the exon/intron region 9 of the gene PLEC1.

As a result, the most efficient RTMs, identified by "Fluorescence Activated Cell Sorting" (FACS) are able to induce endogenous trans-splicing on pre-mRNA level manifested in the fusion of the split GFP pre-mRNA with the 3' exonic sequence of the target gene PLEC1 (see FIGS. 10 and 11 for positions and results of clones).

COL17A1

Similar to PLEC1, after an evaluation of the trans-splicing efficiency by FACS analysis after double transfection of HEK293 cells with single RTM and target molecule, it was surprisingly found that the efficiency for construct PTMN4 (specific for intron 52 of COL17A1) was 79% (i.e. 79% of RTM transfected cells expressed GFP), whereas the efficiency for construct PTMN9 (specific for exon 52 of COL17A1) was 99% (i.e. 99% of RTM transfected cells expressed GFP).

Figure 12:
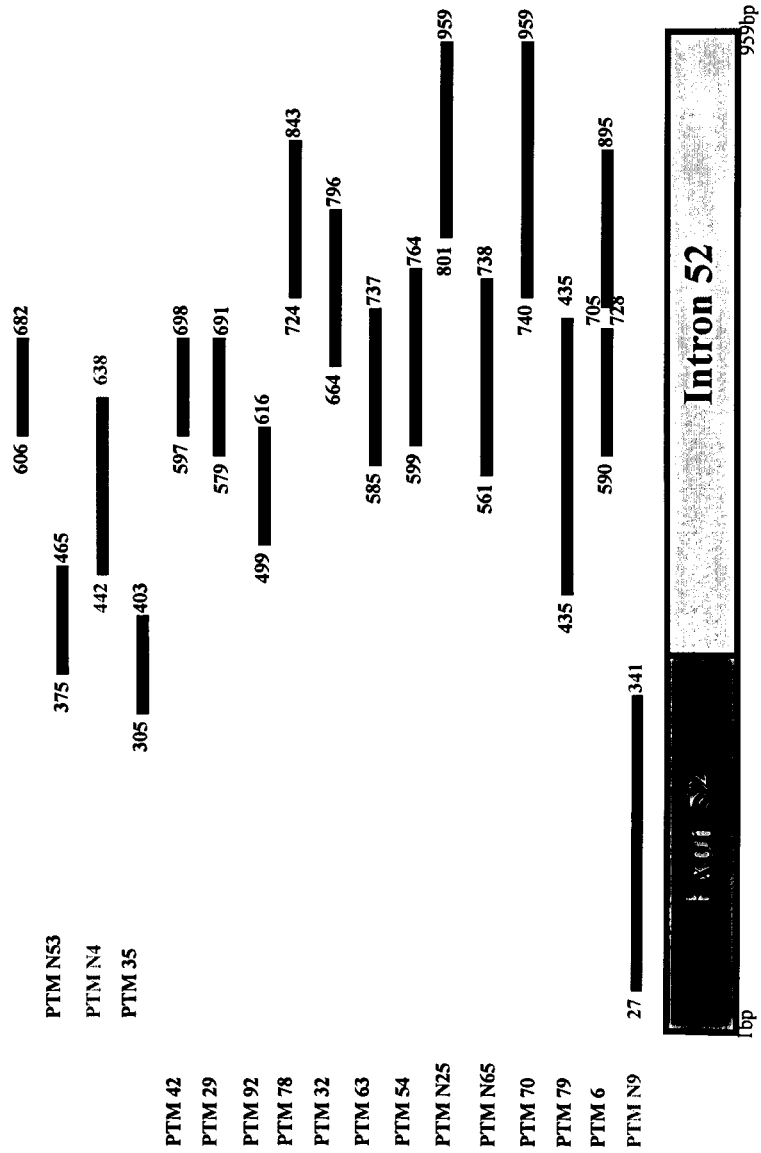
FIG. 12 shows the positions of RTM clones specific for the exon/intron region 52 of the gene COL17A1.

As a result, the most efficient RTMs, identified by "Fluorescence Activated Cell Sorting" (FACS) are able to induce endogenous trans-splicing on pre-mRNA level manifested in the fusion of the split GFP pre-mRNA with the 3' exonic sequence of the target gene COL17A1 (see FIG. 12 for positions of clones). Both genes and experiments provide a proof of concept that exonic sequences provide a more powerful and effective starting point for RTMs according to the present invention.

EXAMPLE 4

Endogenous Trans-Splicing of the Gene of ICAM-1 to IL-10

Figure 13:
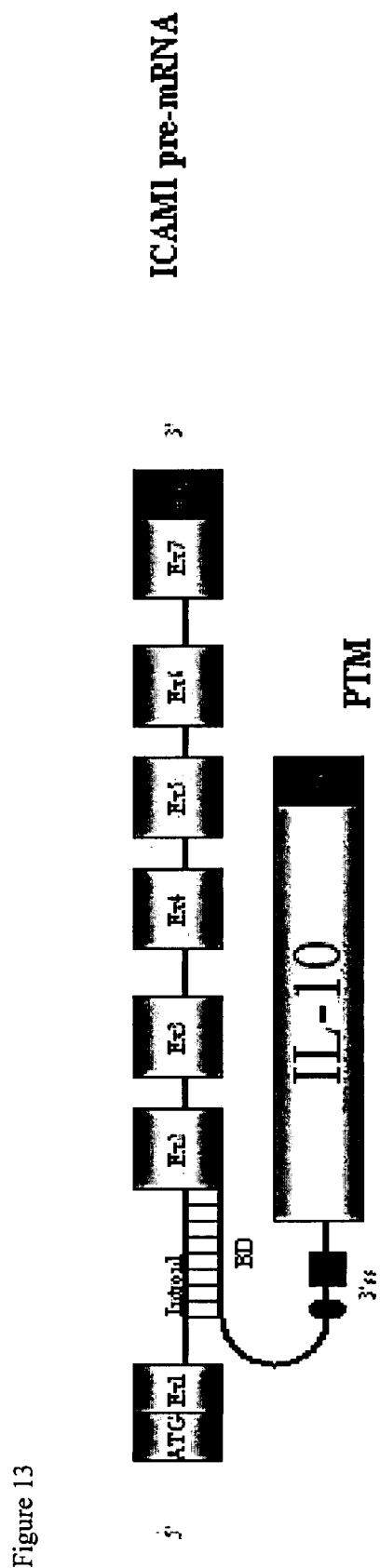
FIG. 13 shows a schematic overview about the RTM construct as produced according to example 4.

FIG. 13 shows a schematic overview about the construct as produced according to this example. The construct of the endogenous RTM was used to analyze for the most efficient binding domains and splice elements for downregulation of ICAM-1 expression and endogenous production of the cytokine IL-10.

18 h after transfection of cells with a RTM containing vector or mock vector HaCaTs were stimulated with TNF-alpha and IFN-gamma to express ICAM-1. After another 26 h real time PCRs were performed in order to detect the endogenous expression of ICAM-1. Furthermore, IL-10 ELISA assays were performed. The results are shown in tables 12 and 13, respectively.

TABLE 12

Transfection of vector containing an RTM with a binding domain for intron 1 of ICAM-1 fused to Il-10 leads to downregulation of ICAM-1: Results real time PCR

|  | endog. RTM without BD with IL-10__26 h | mock (MCS, IRES, Linker)__26 h | endog. RTM 56__26 h | endog. RTM 18__26 h |
|---|---|---|---|---|
| ICAM delta ct | 20.43 | 22.15 | 22.84 | 23.16 |
| ICAM delta delta | 1.72 | 0.00 | −0.70 | −1.02 |
| Fold change | 3.29 | 1.00 | 0.62 | 0.49 |

TABLE 13

Transfection of vector containing an RTM with a binding domain for intron 1 of ICAM-1 and a cDNA coding for leads to expression of IL-10 protein: Results ELISA assay IL-10

|  | Supernatant 11 endog. RTM without BD/with IL-10__26 h | Supernatant 12 mock__26 h | Supernatant 13 endog. RTM 56__26 h | Supernatant 14 endog. RTM 18__26 h |
|---|---|---|---|---|
| OD | 0.054 | 0.033 | 0.189 | 0.063 |
| OD-LW (0.049) | 0.005 | −0.016 | 0.14 | 0.014 |
| IL-10 [ng/ul] | 0 | 0.00 | 164.56 | 7.0625 |

Table legends:
Mock: Transfection with vector containing only multiple cloning site (MCS), internal ribosomal entry site (IRES) and linker
OD: optical density
OD-LW: optical density basic value

The invention claimed is:

1. A pre-mRNA trans-splicing molecule (RTM), comprising
   a) at least one binding domain that targets binding of the molecule to a pre-mRNA expressed within a cell, wherein said binding domain consists of a sequence complementary to an exonic sequence of a mammalian gene;
   b) at least one splicing domain containing motifs necessary for a trans-splicing reaction to occur, and
   c) at least one coding domain, wherein said coding domain encodes at least one exon of a mammalian gene selected from the group consisting of cystic fibrosis transmembrane conductance regulator (CFTR), integrins, TNF-alpha, interleukins, the immunoglobulin superfamily, kallikreins, matrix metalloproteinases, keratins, collagens, and laminins.

2. The RTM according to claim 1, wherein said mammalian gene is selected from the group consisting of the genes plectin, keratin 14, keratin 5, keratin 6, collagen type 7, collagen type 17, laminin A3, laminin B3, g2, integrin β4, a6, CFTR, ICAM-1, and interleukin-10 (IL-10).

3. The RTM according to claim 1, wherein said RTM comprises a coding domain of exons x to y, where x is an integer selected from 1 or 2 to the maximal number of exons, and y is an integer selected from 0 and x+1, with x+1 being limited by the maximal number of exons of said gene.

4. The RTM according to claim 1, wherein said nucleic acid molecule further comprises at least one safety sequence in said splicing domain and/or at least one sequence complementary to a neighboring exon sequence.

5. The RTM according to claim 1, wherein the binding of the molecule to the target pre-mRNA is mediated by complementarity, triple helix formation, or protein-nucleic acid interaction.

6. The RTM according to claim 1, further comprising at least one intron and/or exon, derived from other genes, in order to provide additional desired functionalities, and/or wherein the exon to be trans-spliced comprises naturally occurring or artificially introduced stop-codons in order to reduce gene expression or contains other sequences which produce an RNAi-like effect.

7. The RTM according to claim 1, further comprising a 3'UTR improving trans-splicing efficiency, expression and/or RNA stability.

8. The RTM according to claim 1, which is a DNA, RNA, DNA/RNA hybrid, or nucleic acid analog molecule.

9. A recombinant expression vector, comprising an RTM according to claim 1.

10. The vector according to claim 9, wherein said vector is a eukaryotic expression vector.

11. The vector according to claim 9, wherein said vector furthermore comprises skin-cell specific regulatory elements for regulating transgene expression.

12. A recombinant skin cell comprising an RTM-molecule according to claim 1.

13. A pharmaceutical preparation, comprising a physiologically acceptable carrier and the RTM according to claim 1.

14. A method for treating a disease of the skin or other epithelia, comprising administering to a patient in need a therapeutically effective amount of a medicament comprising an RTM-according to claim 1.

15. The method according to claim 14, wherein said medicament is applied to the skin or systemic circulation.

16. The method according to claim 14, wherein said disease is selected from epidermolysis bullosa, cystic fibrosis, pachyonychia congenita, autoimmune diseases and cancers of the skin.

17. A method for correcting a genetic defect in a subject comprising administering to said subject an RTM according to claim 1.

18. The method according to claim 17, wherein said correcting comprises reprogramming a gene that plays a specific role in a disease selected from epidermolysis bullosa, cystic fibrosis, pachyonychia congenita, autoimmune diseases and cancers of the skin.

19. The recombinant skin cell, according to claim 12, which is a recombinant keratinocyte, fibroblast or endothelial cell.

* * * * *

UNITED STATES PATENT AND TRADEMARK OFFICE
CERTIFICATE OF CORRECTION

PATENT NO.         : 8,735,366 B2                             Page 1 of 1
APPLICATION NO.    : 13/056449
DATED              : May 27, 2014
INVENTOR(S)        : Johann Bauer et al.

It is certified that error appears in the above-identified patent and that said Letters Patent is hereby corrected as shown below:

In the Specification,

<u>Column 29,</u>
Line 43, "in 204" should read --in 20 µl.--.

Signed and Sealed this
Eighteenth Day of November, 2014

Michelle K. Lee
*Deputy Director of the United States Patent and Trademark Office*